United States Patent
Gianotti et al.

(10) Patent No.: US 11,865,279 B2
(45) Date of Patent: Jan. 9, 2024

(54) PRECUTANEOUS-TRANSLUMINAL METHODS THAT MINIMIZE VESSEL STRESS AND TRAUMA

(71) Applicant: CTI Vascular AG, Neuhausen (CH)

(72) Inventors: Marc Gianotti, Wiesendangen (CH); Lisa Gianotti, Wiesendangen (CH); Stefan Richter, Egling (DE)

(73) Assignee: CTI Vascular AG, Neuhausen (CH)

( * ) Notice: Subject to any disclaimer, the term of this patent is extended or adjusted under 35 U.S.C. 154(b) by 861 days.

(21) Appl. No.: 16/918,713

(22) Filed: Jul. 1, 2020

(65) Prior Publication Data

US 2022/0001149 A1    Jan. 6, 2022

(51) Int. Cl.
*A61M 25/10* (2013.01)
*A61B 17/22* (2006.01)

(52) U.S. Cl.
CPC ........... *A61M 25/104* (2013.01); *A61B 17/22* (2013.01); *A61B 2017/22001* (2013.01); *A61B 2017/22038* (2013.01); *A61B 2017/22062* (2013.01)

(58) Field of Classification Search
CPC .......... A61B 17/22; A61B 2017/22062; A61B 2017/22038; A61B 2017/22001; A61F 2/90; A61F 2/958; A61M 25/104; A61M 2025/1068

See application file for complete search history.

(56) References Cited

U.S. PATENT DOCUMENTS

| | | | | |
|---|---|---|---|---|
| 5,549,551 A | * | 8/1996 | Peacock, III | A61M 25/104 604/103.05 |
| 5,645,560 A | * | 7/1997 | Crocker | A61M 25/1029 606/108 |
| 2005/0209674 A1 | * | 9/2005 | Kutscher | A61M 25/1011 623/1.11 |
| 2011/0046985 A1 | * | 2/2011 | Raheman | G06Q 40/08 705/4 |
| 2012/0277718 A1 | * | 11/2012 | Campbell | A61F 2/958 604/99.01 |
| 2015/0051886 A1 | * | 2/2015 | Grady | G06F 18/256 703/2 |

(Continued)

*Primary Examiner* — Jocelin C Tanner
(74) *Attorney, Agent, or Firm* — Olympic Patent Works PLLC

(57) ABSTRACT

The current document is directed to improved PTA methodologies that significantly decrease the risks of persistent blood-vessel-wall distention and subsequent restenosis and the risks of PTA-induced dissection, hematoma, and pseudoaneurysm when used to treat blood vessels. Similar improved percutaneous-transluminal-interventional methods are used to treat non-vascular vessels. The improved methods include initial selection of balloon length and inflation pressure for initial treatment of primary lesions to minimize the risks of over-inflation and generation of undesirable localized forces during balloon inflation. The improved methods further include higher-pressure treatment of remaining secondary lesions that also minimizes the risks of over-inflation and generation of undesirable localized forces. The improved methods can be practiced using differently sized balloons and conventional instrumentation, but may be facilitated by use of balloon-length-adjustable catheters.

20 Claims, 20 Drawing Sheets

(56) References Cited

U.S. PATENT DOCUMENTS

2016/0121087 A1\* 5/2016 Ward .................. A61M 25/104
                                                    606/194
2018/0200490 A1\* 7/2018 Gianotti .............. A61M 25/104
2019/0117090 A1\* 4/2019 Ishii ..................... A61B 5/4836

\* cited by examiner

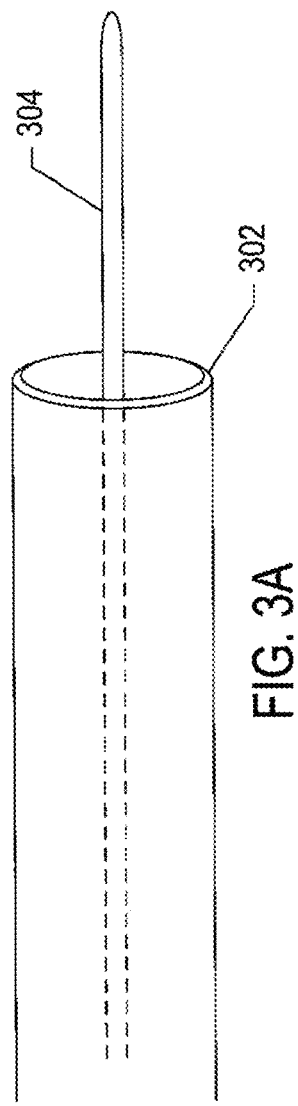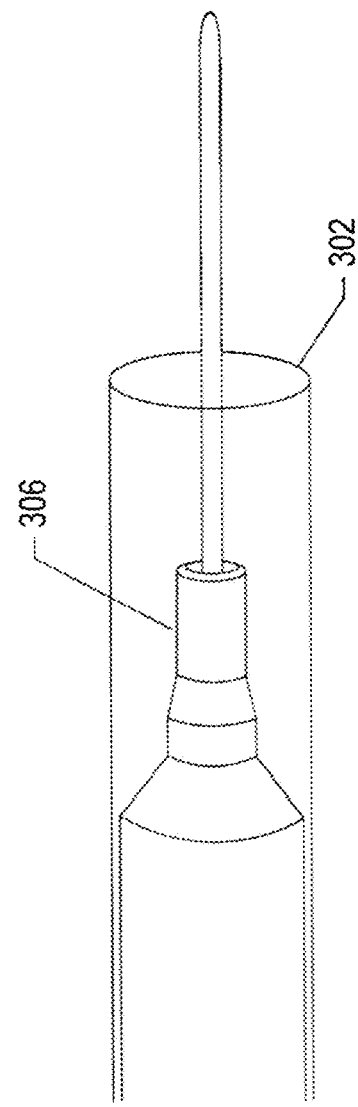
FIG. 3A
FIG. 3B

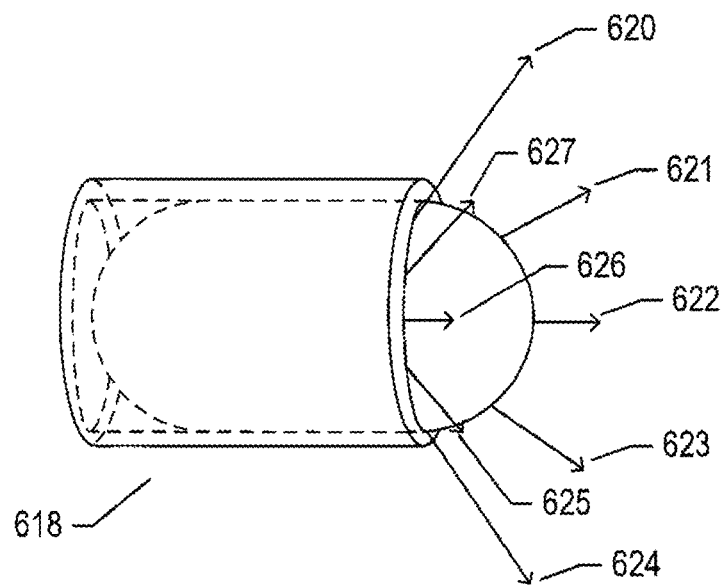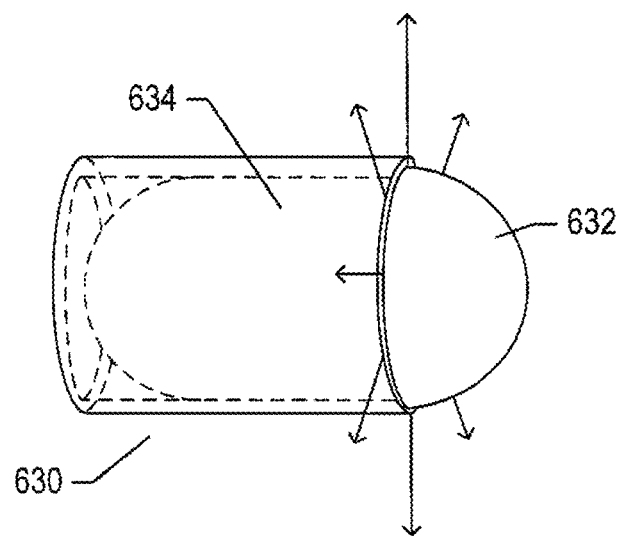
FIG. 6B

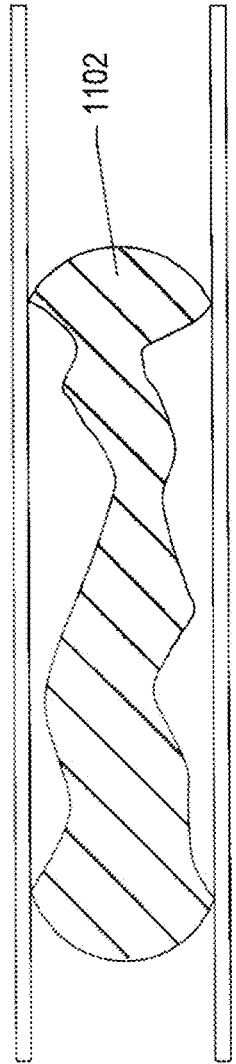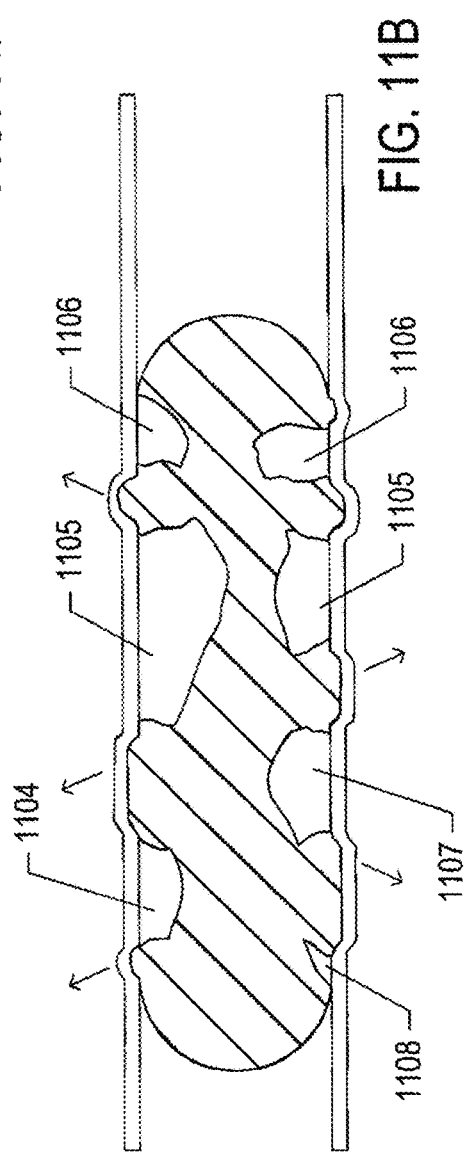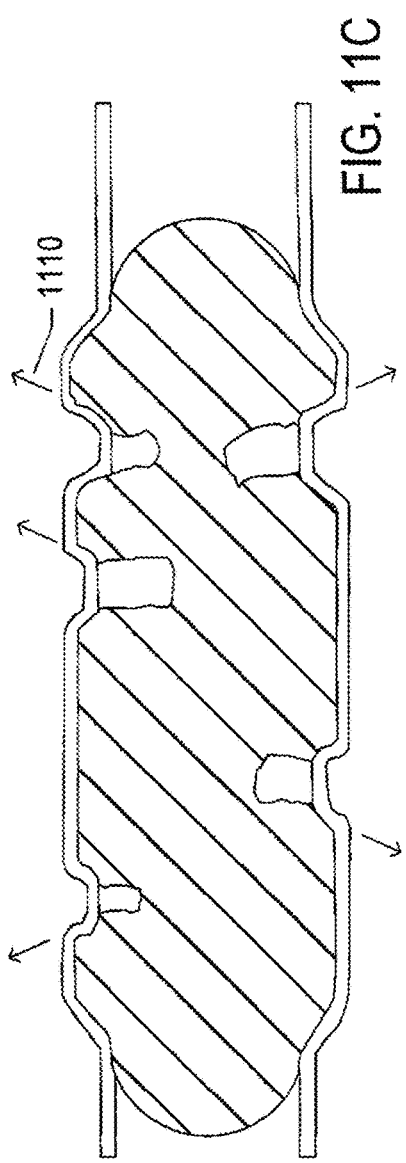

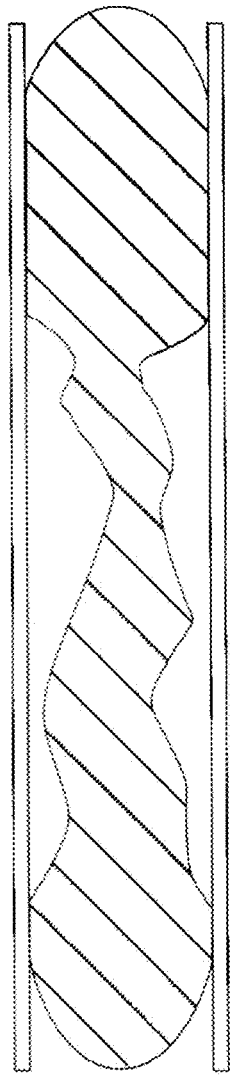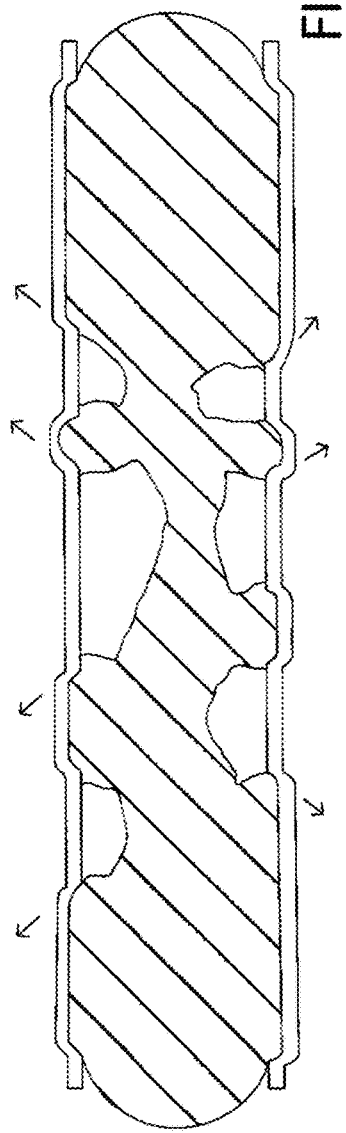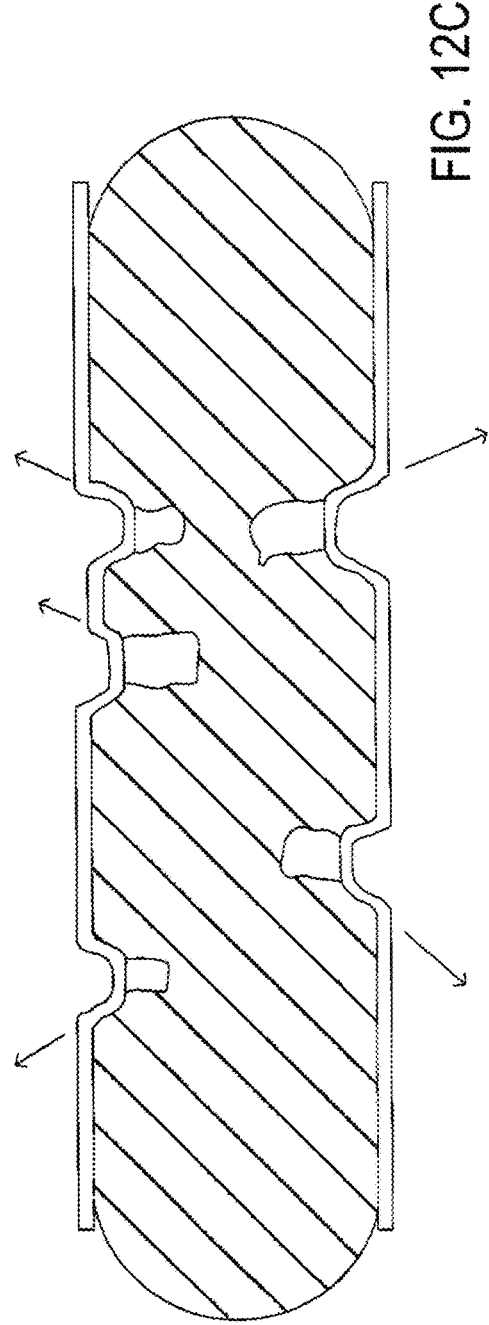

PRECUTANEOUS-TRANSLUMINAL METHODS THAT MINIMIZE VESSEL STRESS AND TRAUMA

TECHNICAL FIELD

The current document is directed to improved methods for treating obstructed arteries, veins, and other vessels within biological tissues, including improved percutaneous-transluminal-angioplasty methods used to treat blood vessels, that improve a family of percutaneous-transluminal methods intended for vascular and non-vascular diseases involving the use of balloon catheters to widen narrowed vessel lumens.

BACKGROUND

Percutaneous transluminal angioplasty ("PTA") refers to methods for widening narrowed blood vessels using balloon catheters. In general, the blood vessels are narrowed by the presence of atherosclerotic plaques that form in the walls of the blood vessels. Atherosclerotic plaques contain lipids, inflammatory cells, smooth muscle cells, and connective-tissue cells and often form in areas of blood-vessel walls exposed to non-laminar or turbulent blood flow, including areas of blood-vessel walls near arterial branch points. The plaques often begin as early atherosclerotic lesions, referred to as "fatty streaks," containing macrophage-induced lipid-laden foam cells formed by uptake of enzymatically oxidized lipids, including oxysterols and 4-hydroxynonenal, from circulating low-density lipoproteins and very-low-density lipoproteins. Macrophages secrete pro-inflammatory cytokines that recruit smooth-muscle cells to the lesion and that stimulate growth of additional macrophages, resulting in growth and development of the early atherosclerotic lesions into subendothelial fibrous plaques with fibrous caps that may, in turn, become calcified. Atherosclerotic lesions are complex matrixes of various types of cells, cell remnants, lipids, oxidized lipids, inorganic ions, and even invasive bacteria. Rupture or ulceration of, or trauma to, atherosclerotic lesions leads to blood clots and further lesion growth which, in turn, may obstruct blood flow, referred to as "stenosis," and lead to myocardial infarction.

In PTA methods, a pre-folded and deflated balloon catheter, for PTA methods referred to as a "PTA catheter," is inserted into a blood vessel over a previously inserted guidewire and the deflated balloon is moved over the guidewire into a narrowed portion of the blood vessel while the position of the deflated balloon is monitored by X-ray fluoroscopy or magnetic-resonance-imaging ("MRI"). A pressurized inflation fluid introduced into an inflation port at the proximal end of the PTA catheter then inflates the balloon, which, in turn, expands the blood vessel and disrupts the atherosclerotic lesion. However, application of PTA methods may result in unwanted results and complications. Over-inflation of the balloon can result in undesirable persistent distention of a blood vessel which, in turn, may disrupt laminar blood flow within and near the distention and lead to new atherosclerotic lesions or regrowth of the treated atherosclerotic lesion. Localized forces produced by balloon inflation can also induce fissures and tears in the inner blood-vessel-wall lining that result in blood flow into a false lumen, or channel, between blood-vessel-wall, referred to as "dissection." In more serious cases, these localized forces result in a hematoma or pseudoaneurysm. The use of drug-eluting PTA catheters may decrease the risks of certain types of PTA complications, but complications due to over-inflation and undesirably large local forces produced during balloon inflation remain a significant problem associated with currently practiced PTA methods. For this reason, designers, developers, and vendors of PTA instrumentation as well as PTA practitioners continue to seek improved PTA methods which decrease or eliminate the risks of various types of PTA complications.

Similar problems are encountered with additional types of percutaneous transluminal interventional methods that employ instruments with expandable members for addressing obstructions in non-vascular vessels. Thus, in general, designers, developers, vendors, and users and of percutaneous-transluminal-interventional-method instrumentation continue to seek improved percutaneous-transluminal-interventional methods which decrease or eliminate the risks of various types of percutaneous-transluminal-interventional-method complications.

SUMMARY

The current document is directed to improved PTA methodologies that significantly decrease the risks of persistent blood-vessel-wall distention and subsequent restenosis and the risks of PTA-induced dissection, hematoma, and pseudoaneurysm when used to treat blood vessels. Similar improved percutaneous-transluminal-interventional methods are used to treat non-vascular vessels. The improved methods include initial selection of balloon length and inflation pressure for initial treatment of primary lesions to minimize the risks of over-inflation and generation of undesirable localized forces during balloon inflation. The improved methods further include higher-pressure treatment of remaining secondary lesions that also minimizes the risks of over-inflation and generation of undesirable localized forces. The improved methods can be practiced using differently sized balloons and conventional instrumentation, but may be facilitated by use of balloon-length-adjustable catheters.

BRIEF DESCRIPTION OF THE DRAWINGS

FIGS. 3A-G illustrate inflation of the balloon of a PTA catheter.
FIGS. 6A-B illustrate the types of forces applied to a blood-vessel wall during PTA-balloon inflation.
FIGS. 11A-C illustrate, using the cross-section representation shown in FIG. 10, application of a conventional PTA method to an atherosclerotic lesion.
FIGS. 12A-C illustrate, using the illustration conventions used in FIGS. 11A-C, application of a conventional PTA method to an atherosclerotic lesion using a balloon with a length that significantly exceeds the length of the atherosclerotic portion of the blood vessel.

DETAILED DESCRIPTION

The current document discloses improved percutaneous-transluminal-interventional methods that significantly decrease risks of persistent vessel-wall distention and other problems encountered when traditional methods are used. In this document, improvements to percutaneous-transluminal-angioplasty ("PTA") methods are described, as an example of the more general class of improved percutaneous-transluminal-interventional methods. However, the currently disclosed PTA methods are representative of the entire class of percutaneous-transluminal-interventional methods. The improved PTA methodologies encompass use of a variety of different types of instrumentation and specific treatment procedures tailored for specific patients and lesions.

Figure 1B:
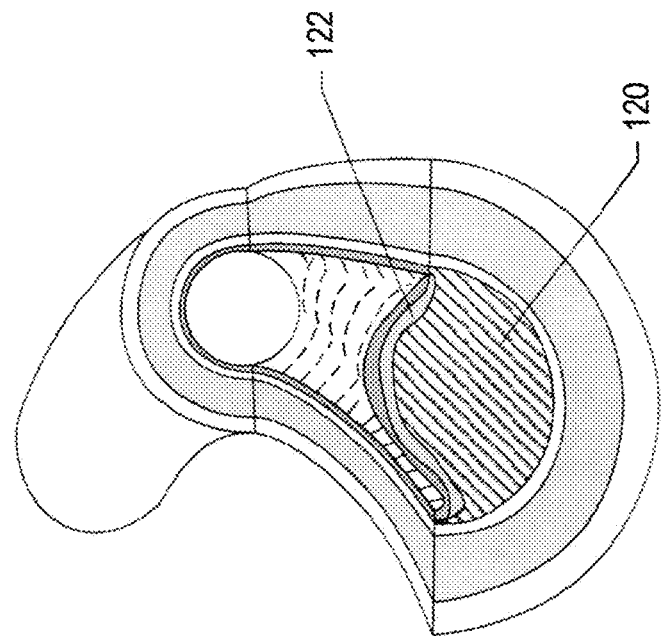
FIGS. 1A-B illustrate an atherosclerotic lesion.
Figure 1A:
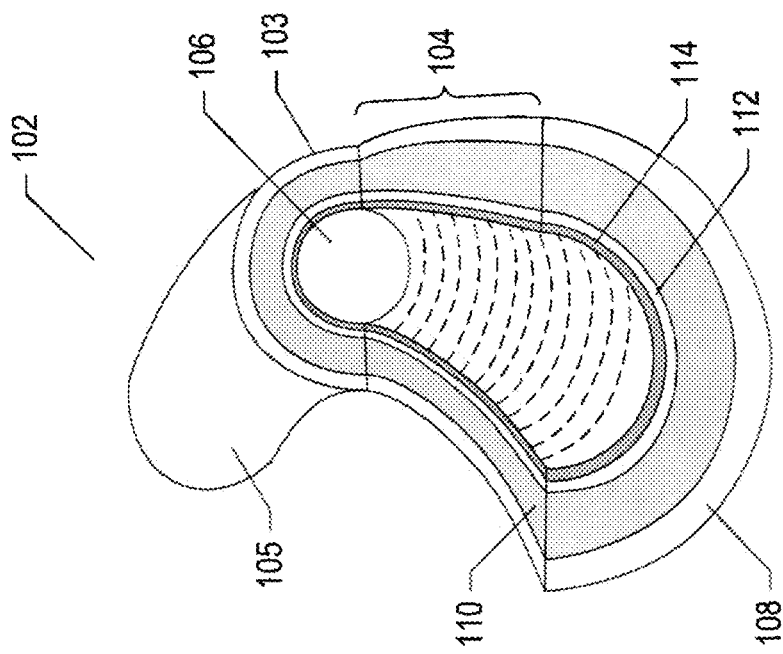

FIGS. 1A-B illustrate an atherosclerotic lesion. FIG. 1A illustrates a portion of a healthy, normal artery. The artery 102 is shown in a cutaway diagram, partly transected 103 and then lengthwise dissected 104. The artery 102 includes an artery wall 105 and an interior lumen 106 through which blood flows. The artery wall includes three main layers: (1) the adventitia 108, comprising several layers of connective tissue that anchor the artery to adjacent, external tissue: (2) the media 110, comprising smooth-muscle cells: and (3) the intima 112, comprising several layers that include an innermost endothelium 114 that forms the inner surface of the artery wall. FIG. 1B illustrates an atherosclerotic lesion. The atherosclerotic lesion 120 occupies a subendothelial volume between the endothelium and internal layers of the intima. As discussed above, the atherosclerotic lesion grows from an initial fatty streak to a complex matrix of various types of cells, cell remnants, lipids, oxidized lipids, inorganic ions, and even invasive bacteria, often capped by a fibrous layer 122 that may become calcified, over time. As also discussed above, PTA methods are used to disrupt the atherosclerotic lesion and reopen the partially or fully occluded arterial lumen.

Figure 2:
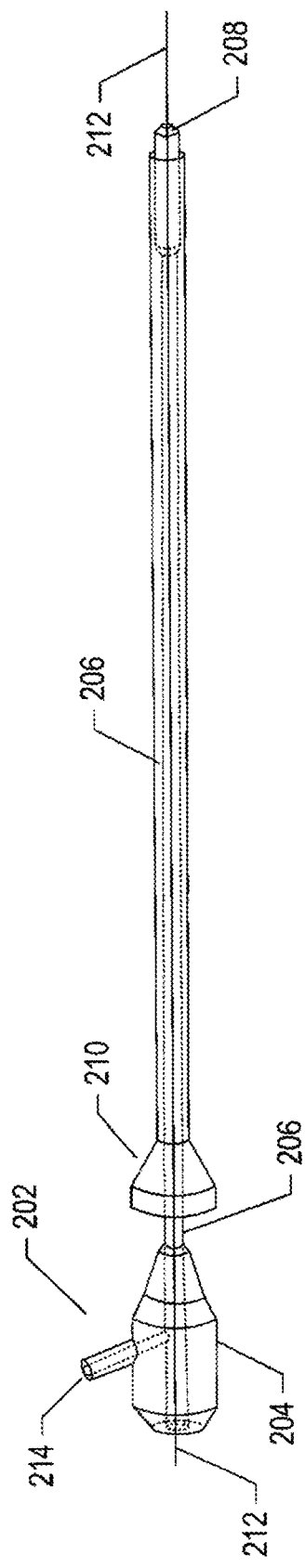
FIG. 2 illustrates a PTA catheter.

FIG. 2 illustrates a PTA catheter. PTA catheters are representative of a more general family of inflatable-member instruments used in general percutaneous-transluminal-interventional methods. The PTA catheter 202 includes a manifold 204, an outer shaft 206, and a deflated balloon 208 at the distal end of the shaft. The shaft of the PTA catheter is shown inserted into the lumen of a support catheter 210 over a guidewire 212. The balloon is inserted into a support catheter when a length-adjustable-balloon configuration is desired or, in certain cases, when additional guidance or shielding of the vessel is desired. Normally, PTA catheters are deployed in the absence of a support catheter. Transradial artery access or transfemoral artery access is used to introduce an introducer sheath into the vascular system. The guidewire is inserted through the introducer sheath and navigated through the vasculature to and past an atherosclerotic lesion to be treated. The support catheter 210 is inserted over the guidewire and navigated to a desired position with respect to the lesion. The PTA catheter is mounted over the guidewire and inserted into the support catheter in order to navigate the balloon to a proper position with respect to the lesion, after which the balloon is inflated by introducing a pressurized liquid, formed from contrast agent and saline solution, into an inflation port 214 that extends from the manifold and that communicates through an outer PTA-catheter lumen to the interior of the balloon.

Figure 3C:
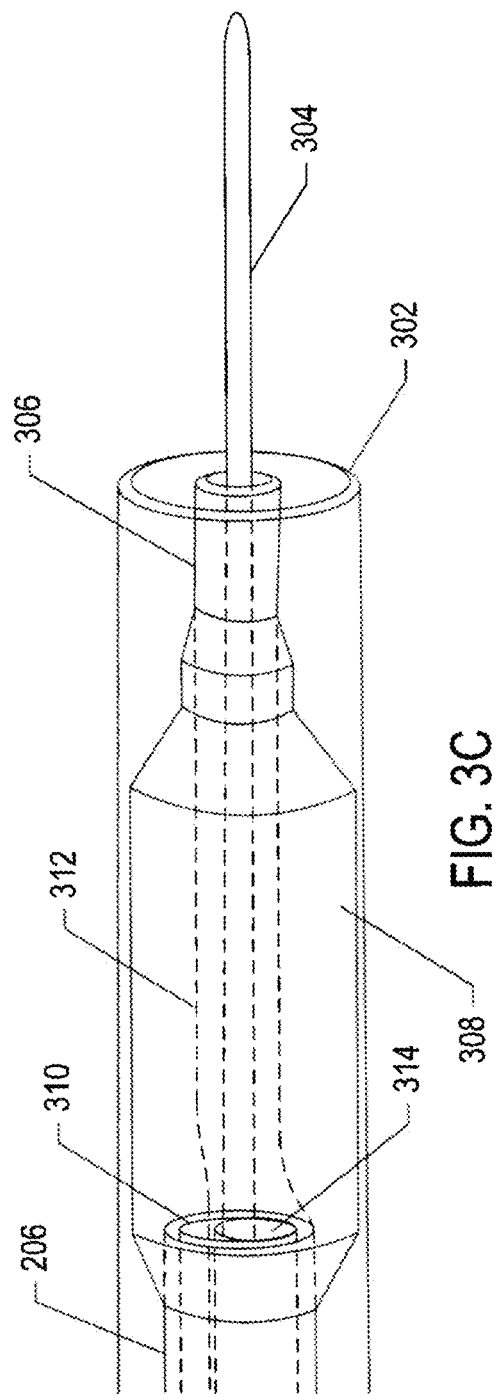

FIG. 3A-G illustrate inflation of the balloon of a PTA catheter. A hypothetical balloon-length-adjustable PTA catheter is used as an example of a PTA catheter, in FIGS. 3A-G but, as discussed above, the currently disclosed improved PTA methodologies can employ traditional PTA catheters as well as balloon-length-adjustable PTA catheters. FIG. 3A illustrates the open, distal end of a support catheter 302 through which a guidewire 304 passes. The distal end of the support catheter is navigated to an appropriate position relative to the lesion to be treated. As shown in FIG. 3B. the distal end of the shaft of a PTA catheter 306 is advanced along the guidewire towards the distal end 302 of the support catheter. As shown in FIG. 3C, the distal end of the PTA catheter 306 is advanced further along the guidewire to a point that it is flush with the distal end 302 of the support catheter. The deflated balloon 308 is fully visible in this figure. The inflation fluid is introduced into the inflation port (214 in FIG. 2) and flows under pressure through a PTA-catheter lumen 310 within the PTA-catheter shaft 206 that is in open communication with the balloon 308. The PTA-catheter shaft 206 further extends into a distal shaft portion 312. The guidewire 304 passes through an inner lumen 314 within the PTA-catheter that is not in fluid communication with the PTA-catheter inflation lumen.

Figure 3D:
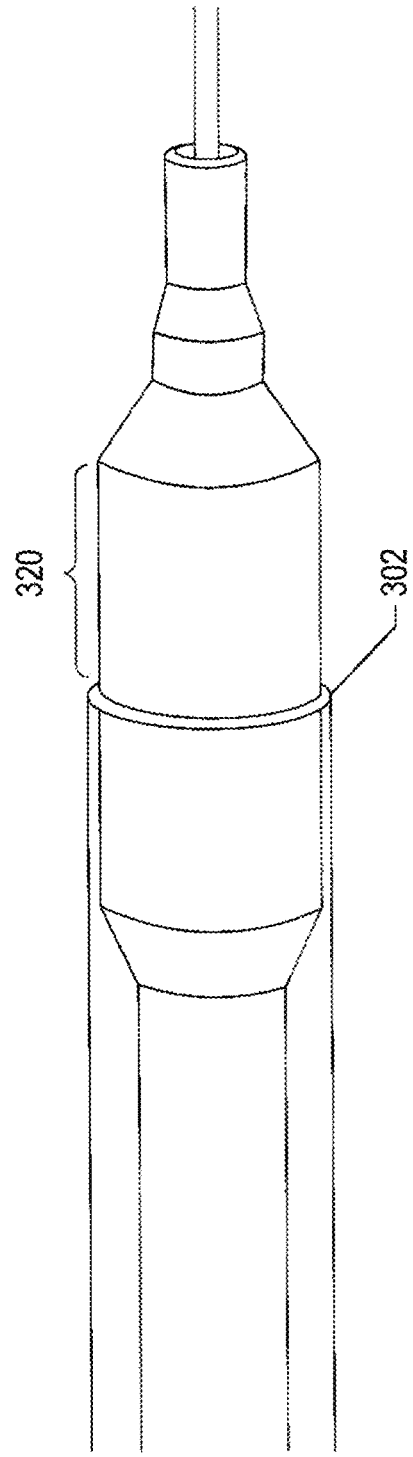
Figure 3E:
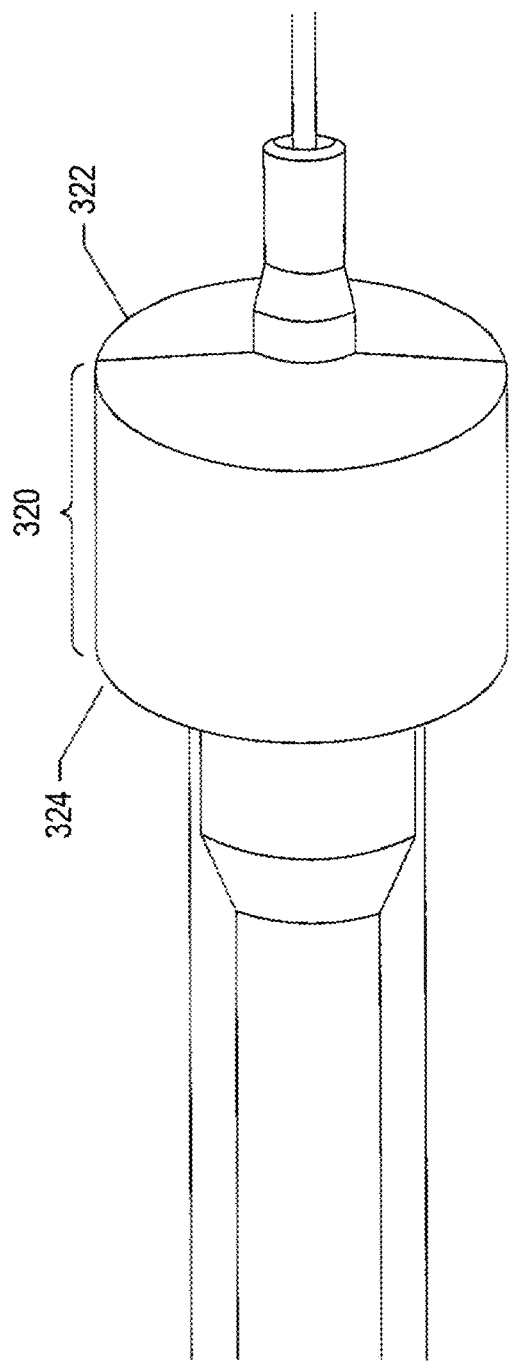
Figure 3F:
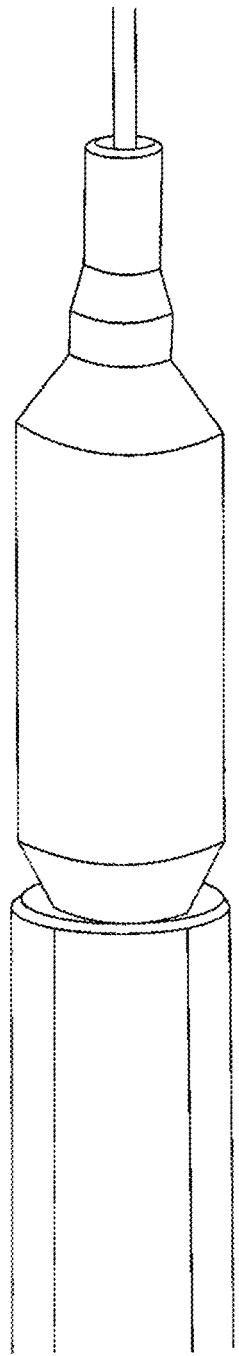
Figure 3G:
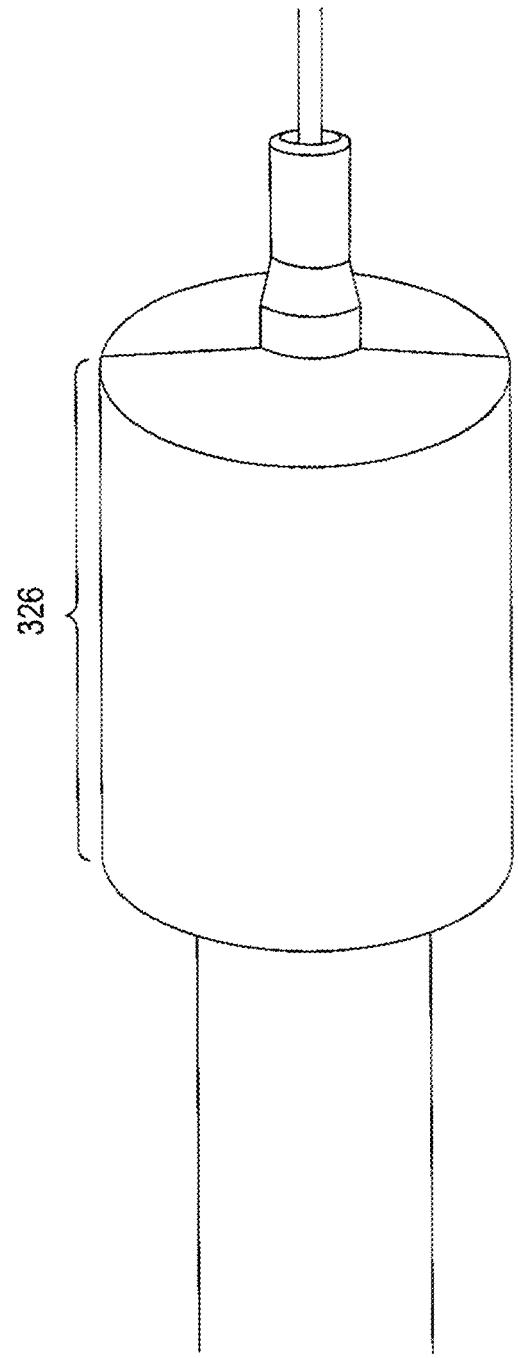

As shown in FIG. 3D, the PTA catheter is further advanced, along the guidewire. so that a desired length, or portion, of the balloon 320 is exposed, past the distal end 302 of the support catheter, to the interior environment of the blood vessel. The inflation fluid is then introduced into the PTA-catheter inflation lumen and pressurized in order to inflate the portion of the balloon exposed to the interior environment of the blood vessel, as shown in FIG. 3E. In this depiction, the inflated balloon appears cylindrical, with relatively sharp edges 322 and 324 at the balloon shoulders, to emphasize the length of the inflated portion of the balloon. However, in real-world instruments, the inflated portion of the balloon has a rounded shape, as shown in a subsequent figure. In FIG. 3F, the deflated balloon is further advanced along the guidewire, prior to inflation, so that the full length of the balloon can be subsequently inflated, as shown in FIG. 3G. Thus, the length 326 of the inflated a balloon can be adjusted by positioning of the distal end of the PTA catheter shaft relative to the distal end of the support catheter. In conventional PTA instrumentation, the balloon is fully inflated in the absence of support catheters as constraining members, and balloon-length adjustment is achieved by selecting, prior to deployment during treatment, one or more PTA catheters, each having a balloon of a different, but constant, length.

Figure 4A:
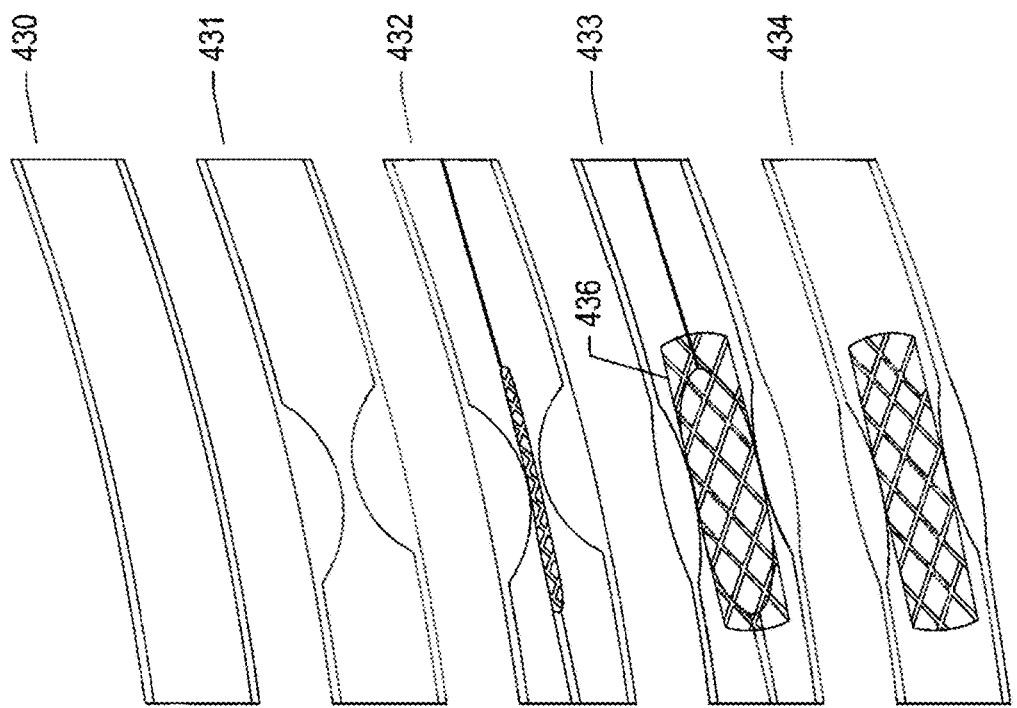
FIGS. 4A-B illustrate two different types of PTA procedures, one type involving the use of a balloon and the other type involving a combination of a balloon with a stent.
Figure 4B:
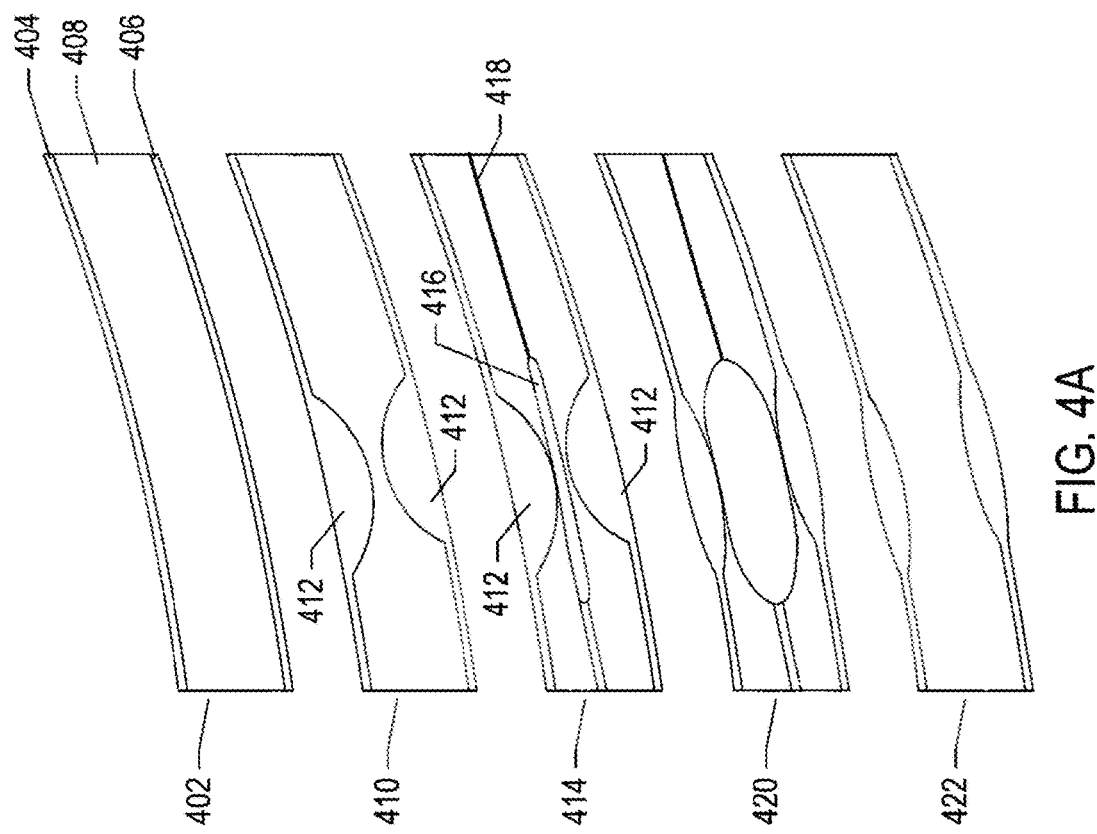

FIGS. 4A-B illustrate two different types of PTA procedures, one type involving the use of a balloon and the other type involving a combination of a balloon with a stent. In each of FIGS. 4A-B, a series of blood-vessel cross-sections are shown. A first blood-vessel cross-section 402 shown in FIG. 4A represents the cross-section of a normal blood vessel, including cross-sections 404 and 406 of the cylindrical blood-vessel wall and a cross-section 408 of the blood-vessel lumen. Cross-section 410 represents a cross-section of a diseased blood-vessel with an annular atherosclerotic lesion 412. Cross-section 414 illustrates a deflated balloon 416 of a PTA catheter inserted over guidewire 418 into the lumen of the diseased blood vessel surrounded by the annular atherosclerotic lesion 412. In cross-section 420, the inflation fluid is pressurized to inflate the balloon, forcing the annular atherosclerotic lesion outward to widen the diseased-blood-vessel lumen and to compress and disrupt the atherosclerotic lesion. Finally, as shown in cross-section 422, the guidewire and PTA catheter are removed, leaving behind a widened, treated blood vessel. A similar procedure is illustrated in cross-sections 430-434. However, in this second procedure, a stent 436 is expanded by inflation of an underlying balloon and left in place, as shown in cross-section 434, following deflation and removal of the PTA catheter and guidewire. The stent is used to support and hold open the blood vessel following application of the PTA method and it may be coated or impregnated with various drugs that are eluted, over time, to inhibit restenosis.

Figure 5A:
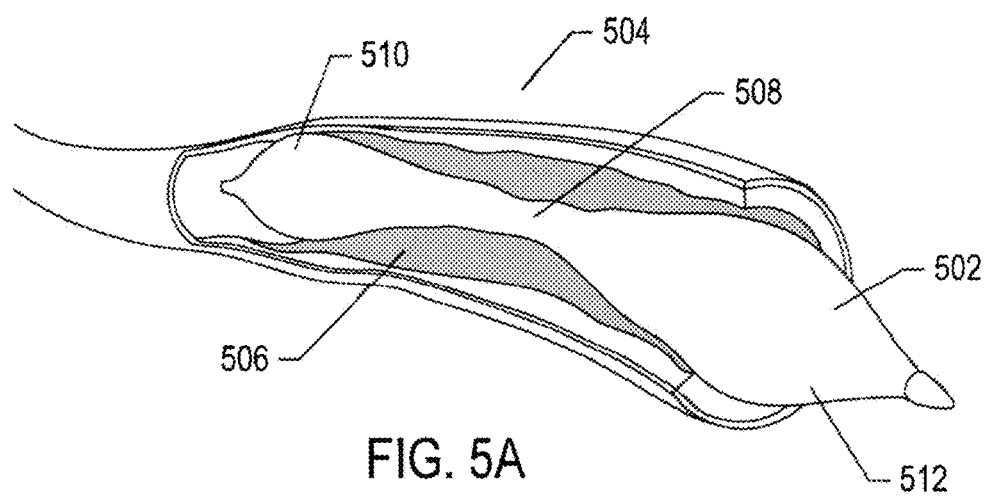
FIGS. 5A-B illustrate certain of the problems that may develop during and after a PTA procedure.
Figure 5B:
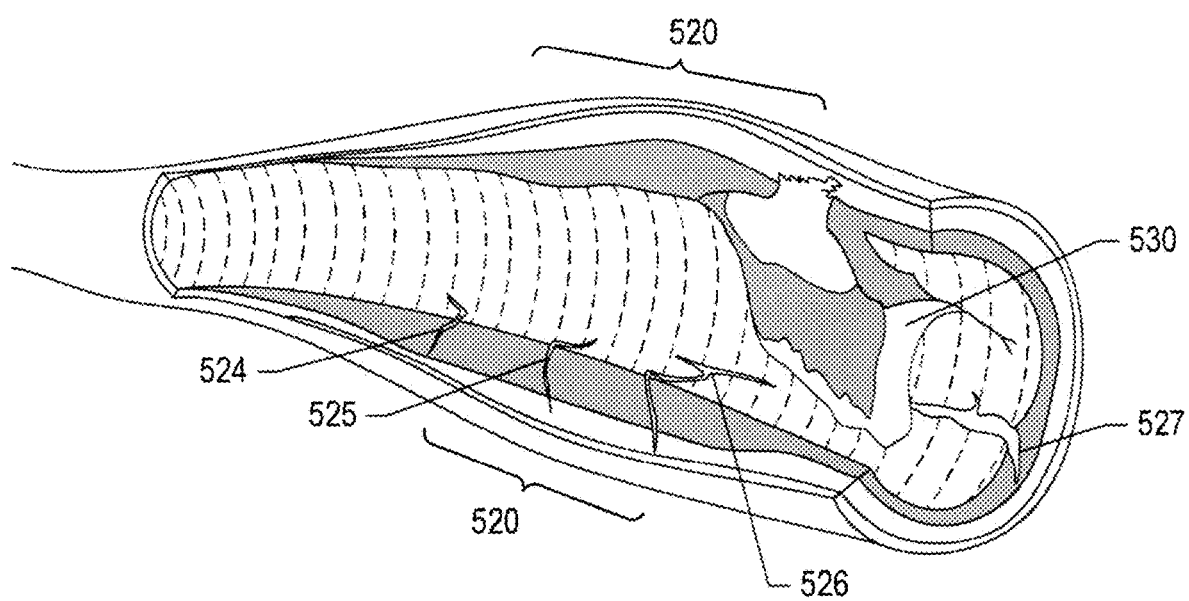

FIGS. 5A-B illustrate certain of the problems that may develop during and after a PTA procedure. FIG. 5A shows an inflated angioplasty balloon 502 within a lesion-containing portion of a blood vessel 504. The lesion 506 is shown shaded in the cross-section of the blood vessel. Note that the inflated balloon, as discussed above, is rounded, rather than cylindrical, as depicted in FIGS. 3E and 3G. Note also that the annular atherosclerotic lesion resists outward displacement by the inflated balloon so that the radial diameter of the balloon is substantially smaller in a middle region 508 within the thickest portion of the lesion and larger 510 and 512 at the proximal and distal ends of the lesion.

FIG. 5B illustrates several deleterious effects of the PTA procedure, following deflation and removal of the PTA balloon catheter. A first deleterious effect is distention of the blood-vessel wall in a portion of the blood vessel overlying the treated atherosclerotic lesion. When a blood vessel is distended to a diameter greater than the normal blood-vessel diameter, the blood-vessel wall may be weakened and the diameter of the lumen persistently increased to the point that blood flow within the widened lumen and upstream and downstream from the widened lumen may become non-laminar and turbulent. Non-laminar and turbulent blood flow, over time, can induce development of additional atherosclerotic lesions as well as result in regrowth of the treated atherosclerotic lesion. A second deleterious effect shown in FIG. 5B are small fissures, or microfissures, in the endothelium and underlying plaque, such as fissures 524-527 that may extend all the way down into the media layer of the blood-vessel wall. These fissures may result in the above-mentioned dissections and may even result in hematomas or pseudoaneurysms. A third deleterious effect shown in FIG. 5B is that portions 530 of the blood-vessel wall may tear away from the blood-vessel wall leaving deep wounds in the blood-vessel wall and resulting in partial blockage of the blood vessel. An additional procedure, such as stenting, is often needed to repair this type of injury. The improved PTA methodologies disclosed in the current document significantly decrease the risks of these types of deleterious effects.

Figure 6A:
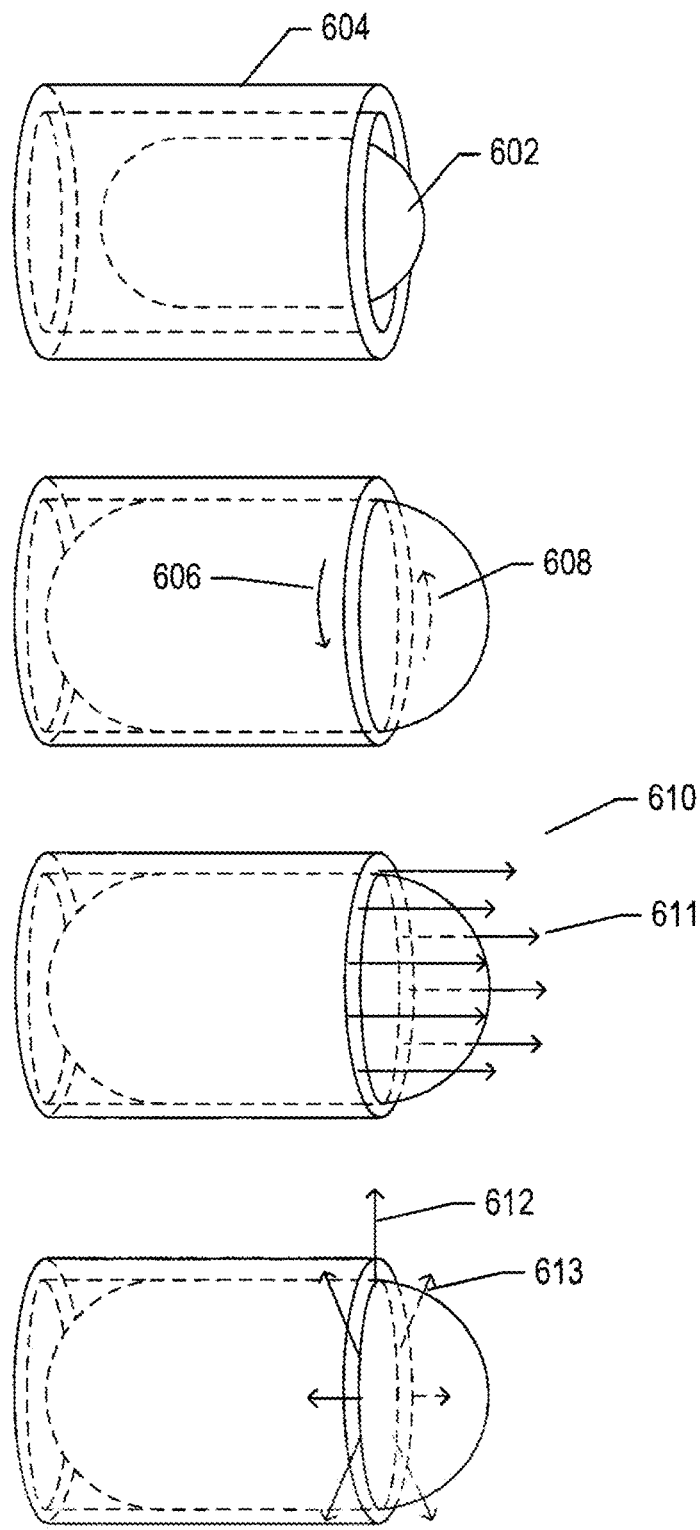

FIGS. 6A-B illustrate the types of forces applied to a blood-vessel wall during PTA-balloon inflation. At the top of FIG. 6A, a small partially inflated angioplasty balloon 602 issue shown within a short cylindrical section of a blood vessel 604. When the angioplasty balloon is inflated to a diameter slightly greater than the internal diameter of the blood-vessel lumen, the angioplasty balloon begins to exert various types of forces on the blood-vessel wall. These include shear forces represented by curved arrows 606 and 608, lateral, axial forces represented by horizontal arrows, including arrows 610 and 611, and radial forces indicated by radially directed arrows, such as arrows 612 and 613. The shear forces may be clockwise or counterclockwise, depending on internal forces within the balloon, balloon stiffening, and the geometry of the constraining blood-vessel-wall surfaces that tend to twist the balloon about its axis of symmetry. The lateral forces arise from friction between the surface of the balloon and the inner surface of the blood vessel as the lateral dimension of the balloon increases with increases in the internal pressure of the balloon. The radial forces naturally arise from expansion of the diameter of the balloon outward. As shown at the top of FIG. 6B 618, vector addition of the linear and radial forces exerted by the inflating balloon create angled force lines 620-627 coincident with a funnel-shaped surface extending outward from an annular region of contact between the inflating balloon in the blood-vessel wall outward. The addition of the shear forces would twist the force lines in a counterclockwise or clockwise direction. Note that the forces are shown in FIGS. 6A-B as emanating from the inner, righthand edge of the cylindrical section, for illustration purposes, but similar force lines are generated over the entire area of contact between the balloon surface and the overlying blood-vessel wall.

As shown at the bottom 630 of FIG. 6B, assuming the right-edge of the cylindrical section of the blood vessel to be an actual edge of a relatively rigid cylinder, when the angioplasty balloon is further inflated, so that the diameter of that portion of the balloon 632 that extends out from the relatively rigid cylinder is greater then the diameter of the portion of the balloon within the relatively rigid cylinder 634, the force lines open up from the funnel-like surface to near-radial or radial force lines since the balloon expansion along the edge is radial rather than lateral. As an example, when the angioplasty balloon is inflated within a relatively rigid, annular atherosclerotic lesion, the forces exerted by the angioplasty balloon on the blood-vessel wall at the edge of the relatively rigid atherosclerotic lesion, due to expansion of the less-rigid vessel wall beyond the lesion, may be more steeply inclined towards radial fore lines but with magnitudes greater than the radial forces exerted over the interior surface of the atherosclerotic lesion.

Figure 7A:
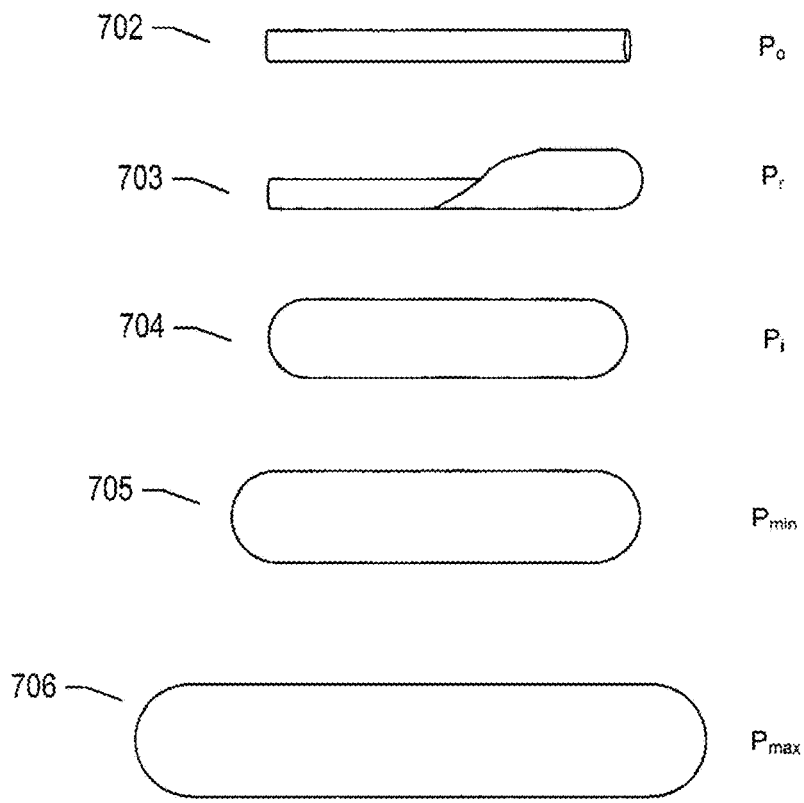
FIG. 7A-B illustrate relationships between angioplasty balloon dimensions and internal balloon pressures.
Figure 7B:
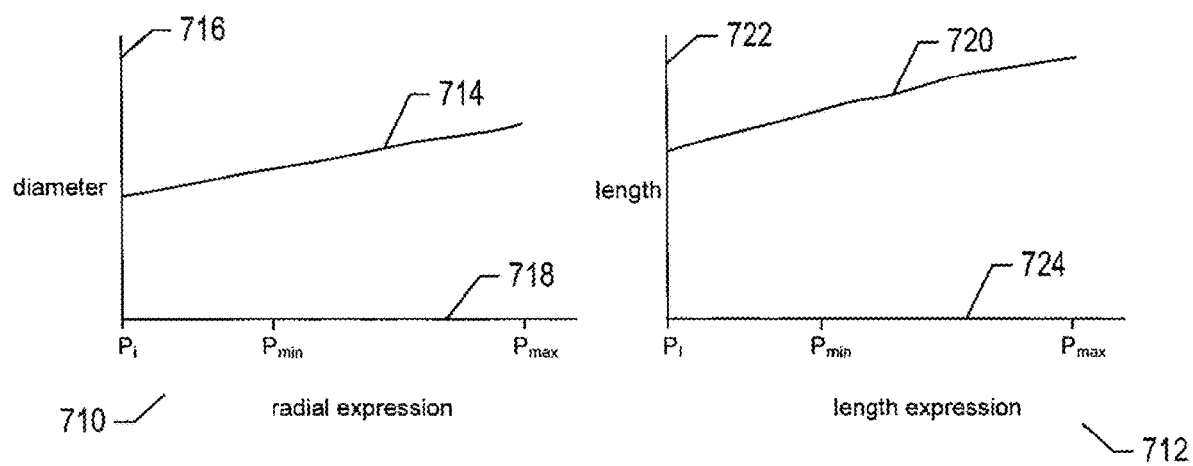

FIG. 7A-B illustrate relationships between angioplasty balloon dimensions and internal balloon pressures. FIG. 7A shows representations 702-706 of an angioplasty balloon at various different internal pressures. In the deflated, folded state 702, the internal pressure of the angioplasty balloon is essentially equal to the ambient, external pressure $P_o$. Inflation fluid is introduced into the balloon at an initial pressure of $P_r$. The initial pressure $P_r$ may be slightly higher than the internal pressure $P_i$ of the balloon when it becomes fully unfolded and has taken a fully inflated shape, represented by state 704 in FIG. 7A. During the initial phase of inflation, as the deflated, folded angioplasty balloon begins to unfold, as represented by state 703 in FIG. 7A, the unfolding balloon may have folds and creases, with various irregularly shaped subvolumes temporarily isolated from one another and having different degrees of resistance against expansion. As result, a somewhat higher initial pressure may be needed to begin the inflation process. During this initial period, large, localized forces may be exerted onto regions of the blood-vessel wall adjacent to folds, creases, and corners in the inflating balloon. After the angioplasty balloon reaches the fully unfolded, fully inflated-shape stage 704, the angioplasty balloon expands regularly and continuously as the pressure is increased from $P_1$ to a maximum allowed pressure $P_{max}$. For each particular PTA procedure, there is generally a minimum therapeutic pressure $P_{min}$ which the angioplasty balloon has expanded sufficiently to begin to apply pressures to the blood-vessel wall sufficient to have a desired therapeutic effect. As the internal pressure the angioplasty balloon is increased from $P_{min}$ to $P_{max}$, both the unconstrained radial and axial dimensions of the angioplasty balloon increase and, when the balloon is constrained by an enclosing structure, such as by the blood-vessel walls, the force exerted by the balloon on the enclosing structure increases.

The rate of unconstrained expansion of an angioplasty balloon with respect to increasing internal pressure can be represented by curves plotted in two-dimensional plots, referred to as compliance charts, and is generally a complex function of the material composition of the balloon, the shape or design of the balloon, the lumen configuration, the fixation points of the balloon, and the thickness of the balloon, which may, of course, vary over the surface of the balloon. FIG. 7B shows a first plot 710 of a radial-expansion curve and a second plot 712 of a lateral, or axial, expansion curve for an angioplasty balloon. The radial-expansion curve 714 is plotted with respect to a vertical, diameter axis 716 in a horizontal, pressure axis 718. Only that portion of the radial-expansion curve between pressures $P_1$ and $P_{max}$ is plotted. The lateral-expansion curve 720 is plotted with respect to a vertical, length axis 722 and a horizontal, pressure axis 724. Only that portion of the lateral-expansion curve between pressures $P_1$ and $P_{max}$ is plotted. In many cases, the curves are near linear. In other cases, the rate of expansion may decrease with increasing pressure. Radial and lateral expansion curves may be available for each of the different angioplasty balloons available to PTA practitioners. When not available, the curves can be estimated, in certain cases, from balloon-material expansion curves and balloon dimensions.

Figure 8:
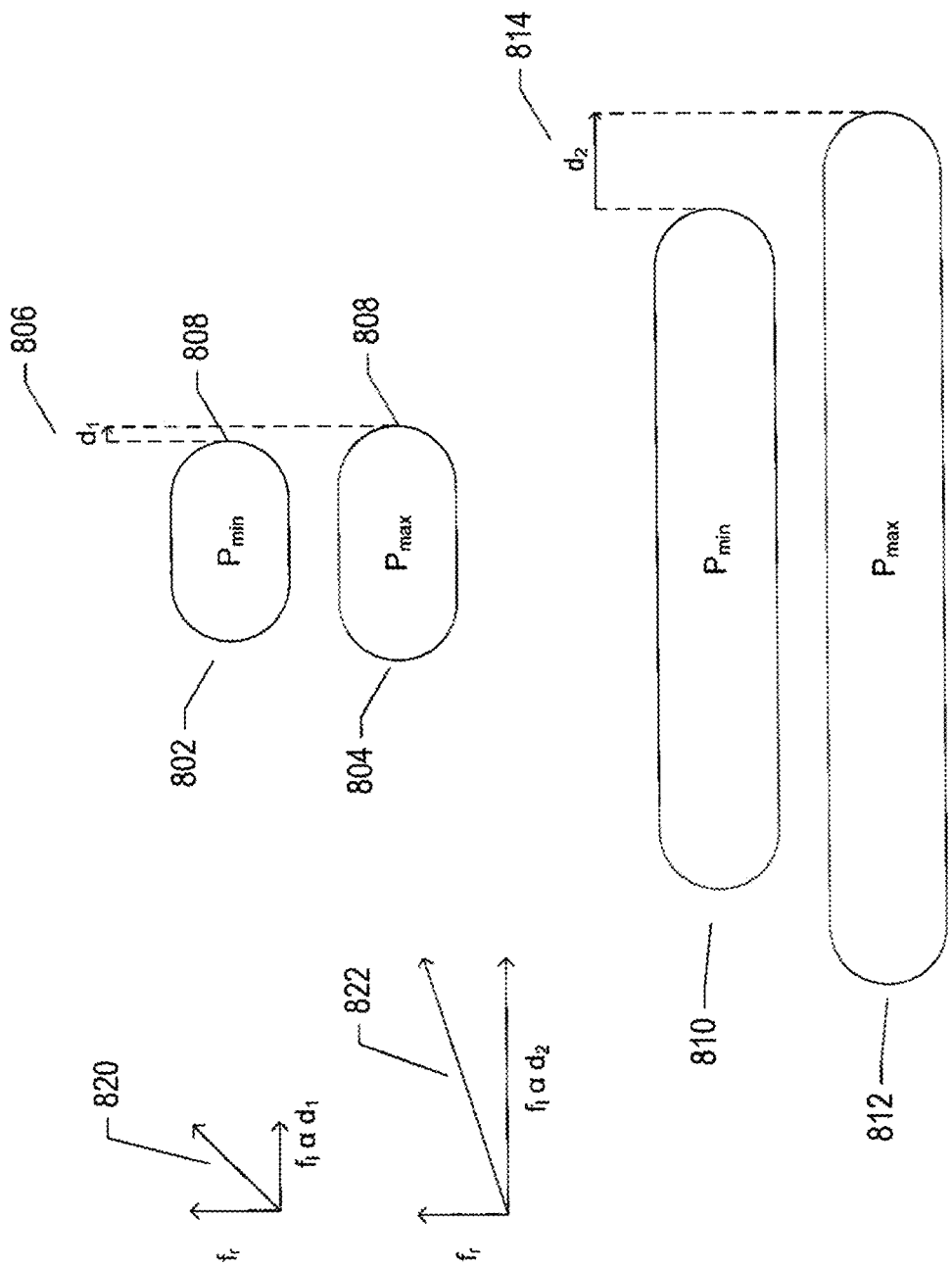
FIG. 8 illustrates the force produced on constraining surfaces by angioplasty balloons of different lengths.

FIG. 8 illustrates the force produced on constraining surfaces by angioplasty balloons of different lengths. Assume, for this example, that the length of a balloon increases by a little over 10% when the internal pressure of the balloon rises from $P_{min}$ to $P_{max}$. In FIG. 8, representations of a relatively short angioplasty balloon at $P_{min}$ 802 and $P_{max}$ 804 are shown with aligned centers, along with the displacement $d_1$ 806 of the rightmost point 808 on the surface of the balloon due to the expansion of the balloon. Representations of a much longer angioplasty balloon at $p_{min}$ 810 and $P_{max}$ 812 are also shown, along with the displacement $d_2$ 814 of the rightmost point on the surface of the balloon. In these figures, radial expansion is relatively small and not illustrated. The radial and lateral forces exerted by the balloon against a constraining surface are generally proportional to the unconstrained displacements of points on the surface of the balloon as the balloon expands. As discussed above, with reference to FIGS. 6B, the radial and lateral forces exerted by the balloon on a constraining surface are components of an overall force obtained by vector addition. For the relatively short balloon, the overall force 820 has a magnitude significantly less than the magnitude of the overall force 800-822 for a long balloon. Thus, in general, the longer the angioplasty balloon, the greater the component lateral forces produced by the balloon against a constraining surface when the internal pressure of the balloon is increased. The magnitudes of the forces exerted by the balloon against a constraining surface may significantly increase at the edges of a constraining surface, and the direction of the forces may also change, as discussed above with reference to FIG. 6B.

Figure 9:
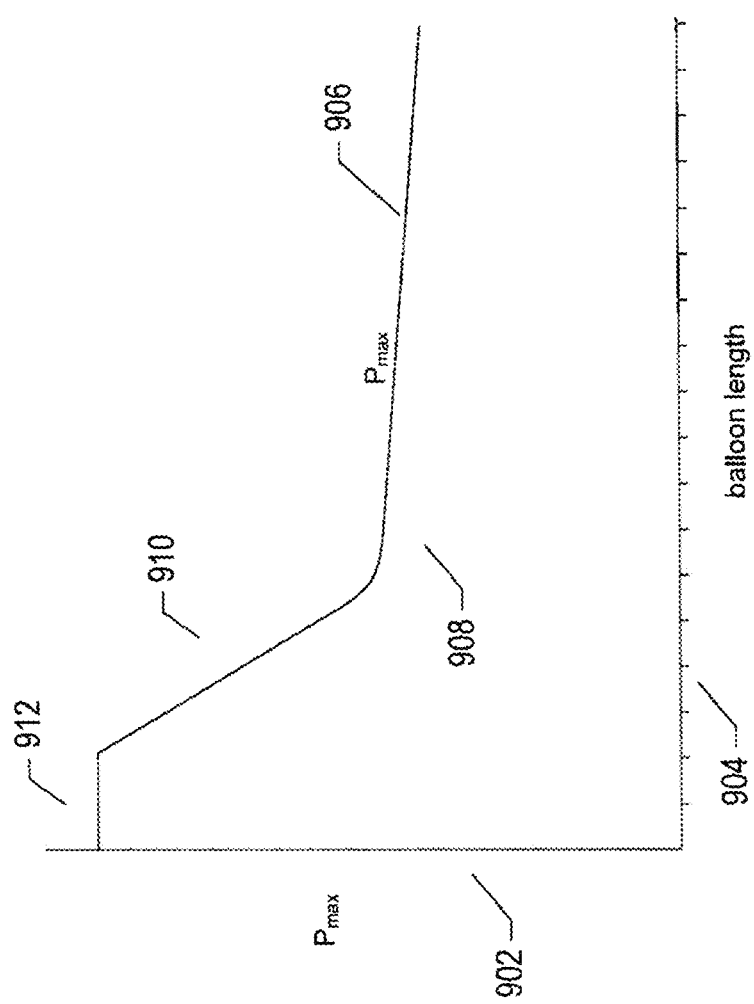
FIG. 9 shows a two-dimensional plot of an example maximum pressure vs. balloon-length curve.

In general, using the radial and lateral expansion curves, material-expansion coefficients and balloon dimensions, and other such data, each different type of balloon is associated with a maximum pressure vs. balloon-length curve. FIG. 9 shows a two-dimensional plot of an example maximum pressure vs. balloon-length curve. The vertical axis 902 represents the maximum usable internal pressure and the horizontal axis 904 represents the balloon length at a reference internal pressure. This may be the balloon length when deflated, the balloon length when unconstrained at the pressure $P_1$, or the length of the balloon at some other reference pressure. The maximum usable pressure increases only slightly with decreasing balloon length in a rightmost portion 906 of the maximum pressure vs. balloon-length curve 908 and then relatively steeply rises in a middle portion 910 of the maximum pressure vs. balloon-length curve before reaching a relatively high-pressure maximum usable pressure plateau 912 at the leftmost portion of the maximum pressure vs. balloon-length curve. The maximum usable pressure is based on the magnitude of the overall force obtained by vector addition of the radial and lateral forces. The above-discussed shear forces may contribute to the magnitude of the overall force, but are often localized and briefly exerted forces that are highly dependent on the geometry of the constraining surfaces and other difficult-to-predict parameters.

Figure 10:
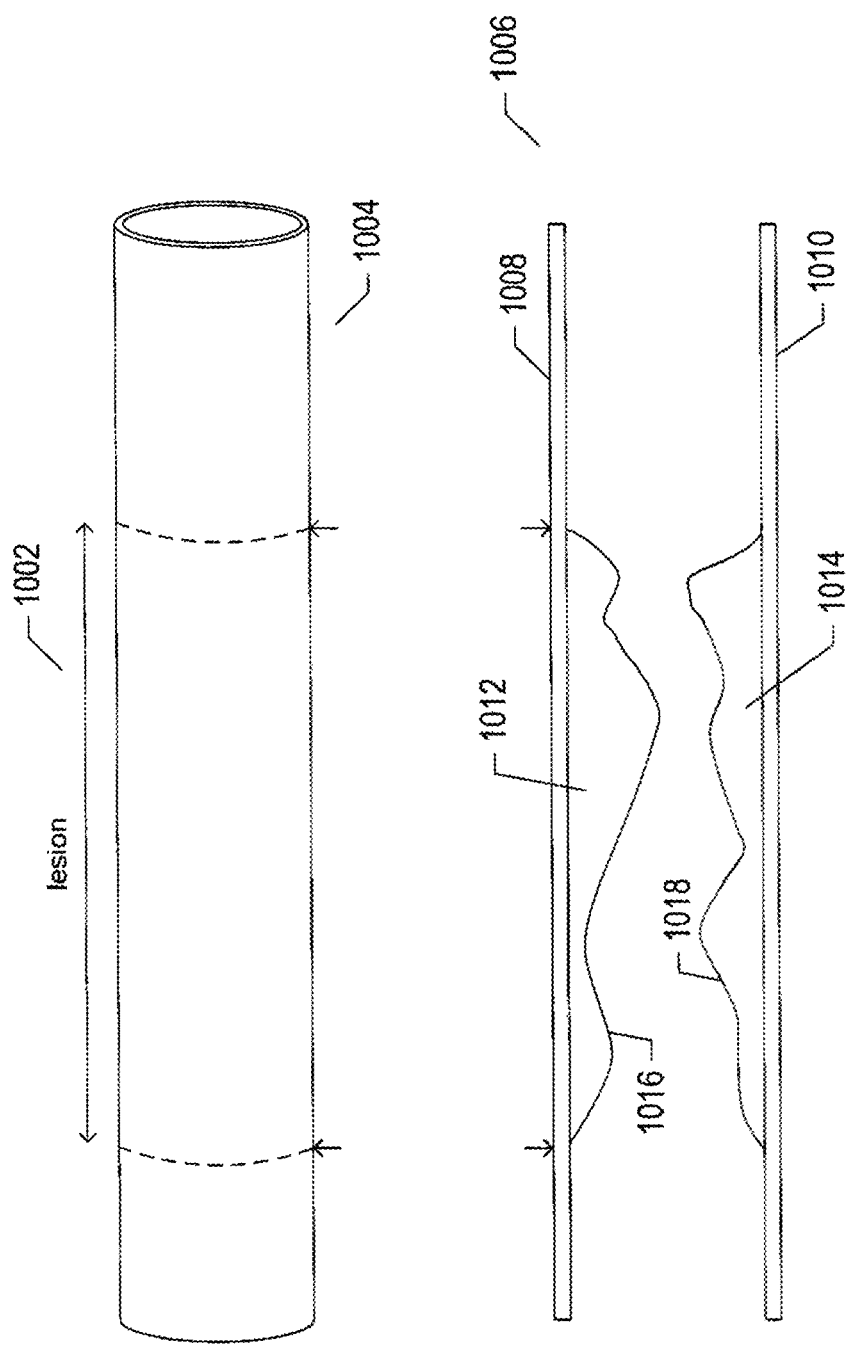
FIG. 10 shows illustration conventions used in FIGS. 11A-13F, which follow.

FIG. 10 shows illustration conventions used in FIGS. 11A-13F, which follow. A representation of a portion 1002 of a longer portion of a blood vessel 1004 containing an atherosclerotic lesion is shown at the top of FIG. 10. A cross-section of the portion of the blood vessel 1006 is shown in the lower portion of FIG. 10, including cross-sections of the blood-vessel wall 1008 and 1010 as well as cross-sections of the somewhat cylindrical atherosclerotic lesion 1012 and 1014. The outer surface of the atherosclerotic lesion is more or less cylindrical, but the inner surface of the lesion 1016 and 1018 is quite irregular.

FIGS. 11A-C illustrate, using the cross-section representation shown in FIG. 10, application of a conventional PTA method to an atherosclerotic lesion. FIG. 11A shows a representation of an angioplasty balloon inflated to an internal pressure $P_1$ within the portion of the blood vessel that includes the atherosclerotic lesion. The cross-section of the volume of the angioplasty balloon is crosshatched 1102 for emphasis. FIG. 11B shows the angioplasty balloon with internal pressure increased $P_{min}$. At this pressure, portions of the lesion have been fractured and displaced, leaving numerous residual, secondary lesions 1104-1108. Note that residual secondary lesion 1105 is annular, as is residual secondary lesion 1106, while residual secondary lesion 1107 is not annular. The areas of the blood-vessel wall between the residual secondary lesions are distended outward, as they are more flexible than the plaque encrusted regions. The internal pressure of the angioplasty balloon is then raised to $P_{max}$n, as shown in FIG. 11C, which results in removal of much of the residual secondary lesions, but which further distends the portions of the blood-vessel walls overlying the angioplasty balloon. Depending on the blood vessel, lesion, and angioplasty-balloon characteristics, distention of the blood-vessel walls at this elevated pressure may result in persistent widening of the blood vessel past its normal width which, as discussed above, may result in non-laminar and turbulent blood flow and a greater chance of restenosis. In addition, forces produced at the edges of the secondary lesions, represented by arrows, such as arrow 1110, may be sufficient to produce dissections and tears of the inner layers of the blood-the vessel walls.

FIGS. 12A-C illustrate, using the illustration conventions used in FIGS. 11A-C, application of a conventional PTA method to an atherosclerotic lesion using a balloon with a length that significantly exceeds the length of the atherosclerotic portion of the blood vessel. FIG. 12A shows the angioplasty balloon inflated to an internal pressure $P_1$. FIG. 12B shows the angioplasty balloon inflated to an internal pressure $P_{min}$, and FIG. 12C shows the angioplasty balloon inflated to an internal pressure $P_{max}$. In this case, distention of the blood-vessel walls at $P_{min}$ and $P_{max}$ is significantly more pronounced and the forces produced at the edges of the residual secondary lesions are much larger, due to the increased overall forces for longer balloons, as discussed above with reference to FIGS. 6B and 8. In this case, the risks of persistent over-widening of the blood vessel, dissection, vessel-wall tears, hematoma, and pseudoaneurysm are significantly higher. However, in both this case in the case shown in FIGS. 11A-C, insufficient pressure is available at $P_{max}$ to completely remove the plaque.

Figure 13A:
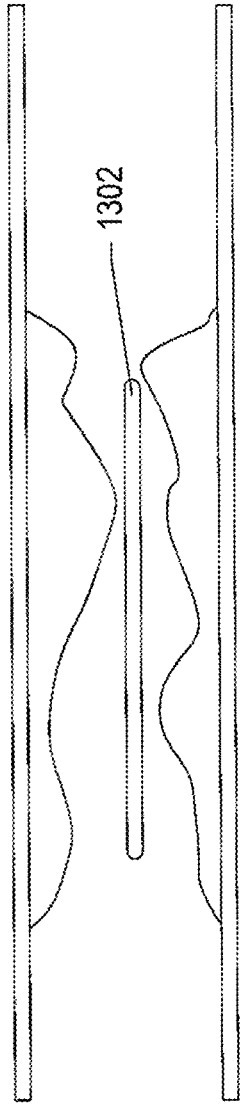
FIGS. 13A-F illustrate the currently disclosed PTA methodology.
Figure 13B:
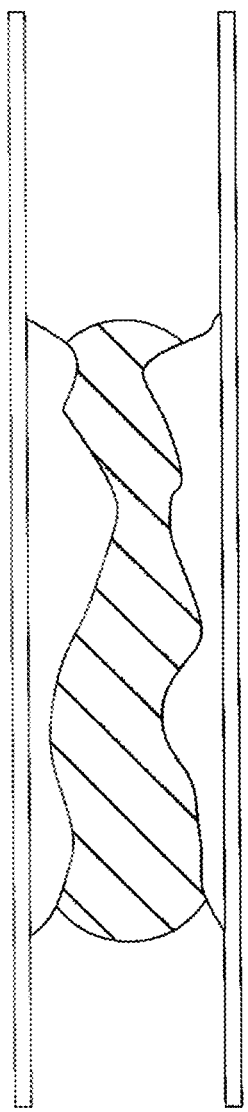
Figure 13C:
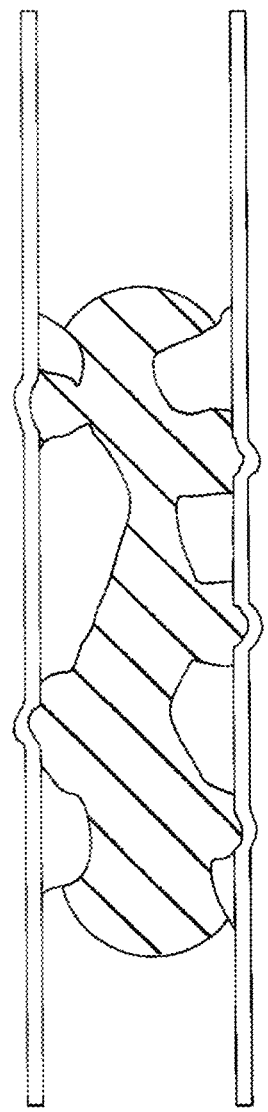
Figure 13D:
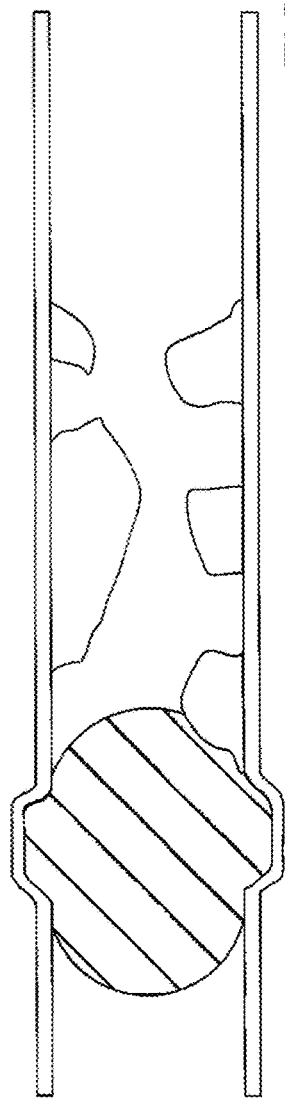
Figure 13E:
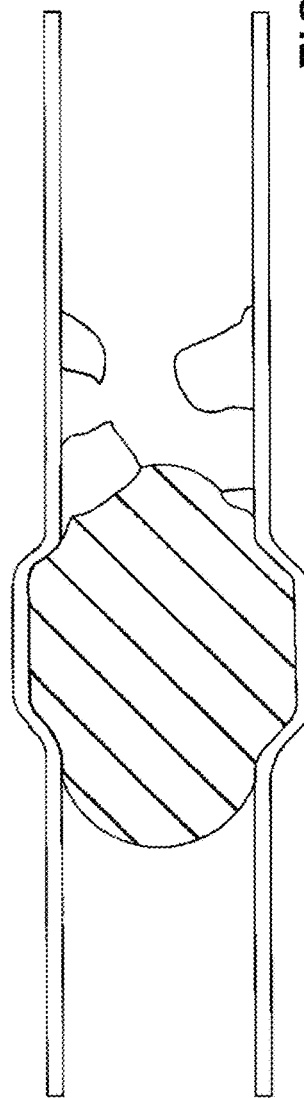
Figure 13F:
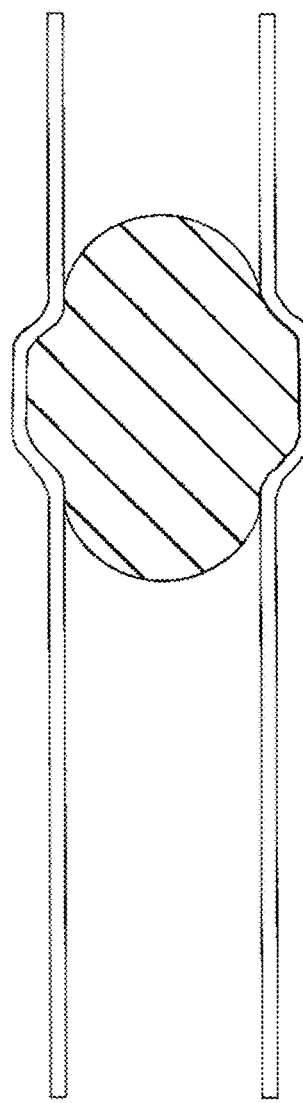

FIGS. 13A-F illustrate the currently disclosed PTA methodology. FIG. 13A shows the deflated angioplasty balloon 1302 centered within the lumen within the atherosclerotic lesion. The length of the angioplasty balloon has been carefully selected so that, when the internal pressure of the balloon is increased to $P_{min}$, the length of the angioplasty balloon will not exceed the length of the plaque-encrusted portion of the blood vessel. The angioplasty balloon is then inflated, very slowly, to $P_1$, as shown in FIG. 13B. Note that the balloon remains well centered within the portion of the blood vessel encrusted with plaque and the length of the balloon does not exceed the plaque-encrusted portion. This prevents the large forces generated at the plaque boundaries when a balloon with a length exceeding those boundaries is used. Slow inflation prevents applying large, localized forces that can be produced by rapid inflation of a deflated and folded angioplasty balloon. The internal pressure of the angioplasty balloon is then raised to $P_{min}$, as shown in FIG. 13C. While this internal pressure is insufficient to dislodge significant portions of the plaque, the pressure is also insufficient to generate forces that result in persistent over-widening of the blood vessel and generation of fissures and dissections. Next, as shown in FIG. 13D, the length of the angioplasty balloon is a shortened, or a shorter angioplasty balloon is selected, so that it corresponds to the dimensions of one or a few residual secondary lesions, and is inflated to a pressure up to $P_{max}$ for the selected balloon length, as needed. As discussed above with reference to FIG. 9, the maximum usable pressure for short balloons is significantly higher than that for longer balloons. Therefore, sufficient force can be applied to the one or a few residual secondary lesions in order to remove or flatten them without generating the deleterious forces that significantly increase the risk of persistent over-widening and dissections. As shown in FIG. 13E, a relatively short balloon length or balloon is selected for treatment of the next one or few residual secondary lesions, and this approach is applied, in FIG. 13F, to a final one or a few residual secondary lesions.

Figure 14A:
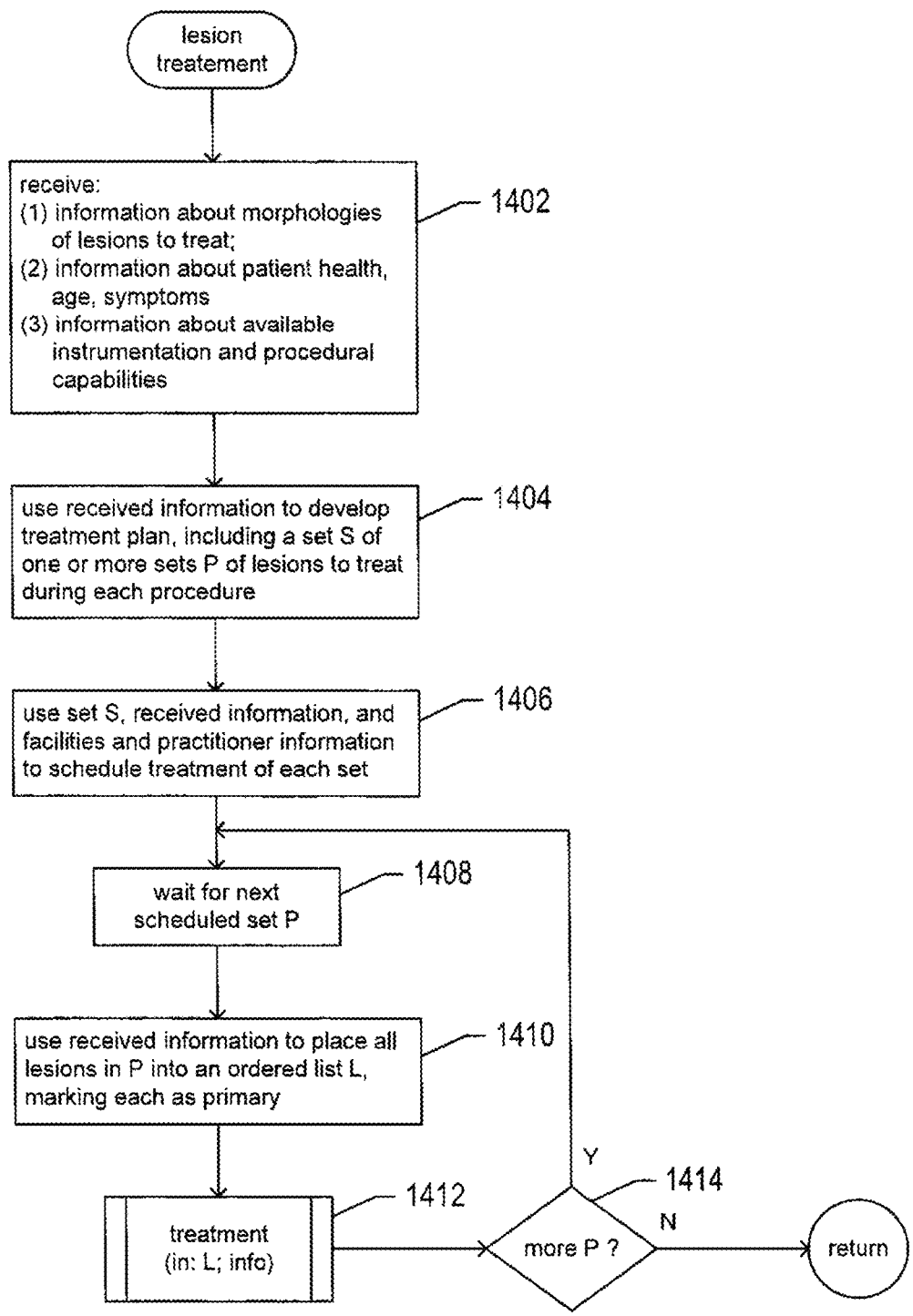
FIGS. 14A-B illustrate the currently disclosed PTA methodologies using a flow-control-like illustration technique.
Figure 14B:
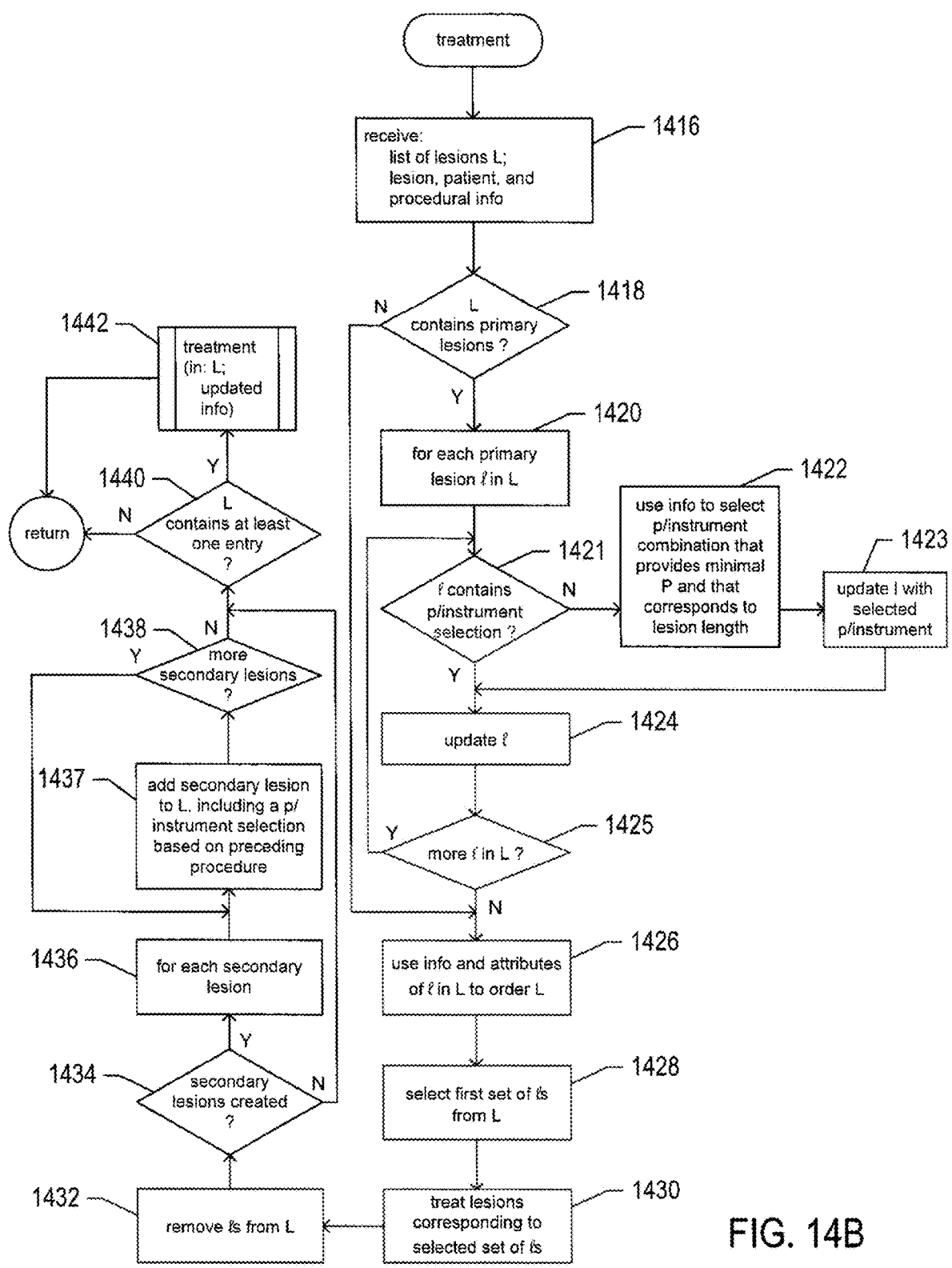

FIGS. 14A-B illustrate the currently disclosed PTA methodologies using a flow-control-like illustration technique. The currently disclosed PTA methodologies can be practiced manually by one or more practitioners, can be practiced semi-automatically, with the one or more practitioners using a computer application to assist them in selecting angioplasty balloons and balloon lengths and pressures, and may, in the future, be automatically or largely automatically applied by machine control of automated PTA instrumentation.

FIG. 14A provides a control-flow diagram for the lesion-treatment method that represents an example of the currently disclosed PTA methodologies. In step 1402, information about the morphologies and other characteristics of the lesions that are to be treated is received, along with information about the patient, the patient's health, the patient's symptoms, and other patient information as well as information about available instrumentation and procedural capabilities. In step 1404, the received information is used to develop a treatment plan, including a set S of one or more sets P of lesions to treat during each PTA procedure. For example, in certain cases, the set S may contain only a single set P with one or more lesions that can all be treated during the same procedure. In other cases, there may be two different lesion-containing locations that need to be treated separately during two different procedures, as a result of which the set S contains two different lesion sets $P_1$ and $P_2$. The grouping of lesions into treatment sets may involve many different considerations, including the physical locations and the types of lesions. types of available instrumentation, patient health, and other considerations. In step 1406, the set S, the information received in step 1402, and information about facilities and practitioners are used to schedule treatment of each set P of lesions. In step 1408, the method waits for the next scheduled treatment time. Once a next scheduled treatment time is reached, the lesions to be treated in the set of lesions P are placed into an ordered list L, with each lesion or entry l in the list L marked as a primary lesion, in step 1410. In step 1412. the lesions are treated via the currently disclosed improved PTA methodologies, represented in FIG. 14A by a call to a treatment routine or method. When there are more procedures to carry out, as determined in step 1414, the method returns to step 1408. Otherwise, the lesion-treatment method terminates.

FIG. 14B provides a control-flow diagram for the treatment method or routine invoked in step 1412 of FIG. 14A. In step 1416, the list of lesions L and the various information discussed above with reference to FIG. 14A are received. In step 1418, the method determines whether the list L contains any primary lesions. If so, then, in the for-loop of steps 1420-1425, each primary lesion l in the list L is considered. When the currently considered primary lesion l is already associated with pressure instrumentation-selection information, as determined in step 1421, that information is reviewed and updated using any additional, relevant information obtained since the pressure/instrumentation-selection information was last updated. Otherwise, in step 1422, a pressure/instrumentation combination is selected to provide application of minimal but therapeutically effective pressure to the primary lesion using an angioplasty balloon having a length that does not exceed the length of the lesion, as discussed above with reference to FIGS. 13A-G. In step 1423, the entry for lesion l in list L is updated using the selections made in step 1422. When there are more primary lesions to consider, as determined in step 1425, another iteration of the for-loop of steps 1420-1425 is carried out. Otherwise, in step 1426, the lesion entries l in the list L are reordered using the updated information associated with each entry. The ordering of the lesions may involve a variety of different considerations, including their positions within a blood vessel, their types, the therapeutic pressures needed to be applied, and other such considerations. In step 1428, a set of one or more list entries representing lesions to treat during the next step of the procedure is selected from the ordered list L. In general, the selected lesions are close to one another and have sufficiently similar characteristics to be treated together, with an appropriately selected balloon length and internal balloon pressure. In step 1430, the selected lesions are treated using an internal balloon pressure and balloon length determined from the pressure and instrumentation selections associated with the list entries representing the lesions. In step 1432, the entries representing the treated lesions are removed from the list L. When residual secondary lesions remain following treatment in step 1430, as determined in step 1434, each residual secondary lesion is considered in the for-loop of steps 1436. In step 1437, the currently considered residual secondary lesion is added to the list L, along with a pressure/instrumentation selection based on the pressure used in the treatment in step 1430, observed characteristics of the residual secondary lesion, and other considerations. In general, as discussed above, shorter angioplasty balloons are selected in order to treat residual secondary lesions at higher pressures while avoiding significant risks of persistent overwidening of the blood vessel and dissections. If there are more residual secondary lesions to consider, as determined in step 1438, flow returns to step 1437. Otherwise, when the list L contains at least one entry, as determined in step 1440, the treatment method or routine is recursively called in step 1442 to continue treating any lesions remaining to be treated. When the list L is empty, the treatment method terminates.

Although the present invention has been described in terms of particular embodiments, it is not intended that the invention be limited to these embodiments. Modifications within the spirit of the invention will be apparent to those skilled in the art. For example, the decision processes involved in selecting sets of lesions to treat during each procedure and ordering treatment of lesions during each procedure may be complex and differ significantly from procedure to procedure, depending on a variety of factors and conditions. As discussed above, the currently disclosed methods can be used with different types of PTA instrumentation. As also discussed above, pressure and instrumentation selections may be based on the balloon-characteristics information on hand, including compliance curves, material compliance coefficients, balloon and lumen geometries and associated computational methods, and other such information. The currently disclosed PTA methods are representative of an entire class of improved percutaneous-transluminal-interventional methods.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A method that treats a lesion within a vessel lumen of a patient, the method comprising:
    selecting an adjustable-balloon-length balloon catheter;
    preparing the patient to receive the adjustable-balloon-length balloon catheter;
    selecting a balloon length that does not exceed the length of the lesion when a selected balloon of the selected length is inflated to a first treatment pressure $P_{min}$;
    centering the selected balloon at the distal end of the balloon catheter within a portion of a vessel lumen containing the lesion;
    raising an internal pressure of the selected balloon to $P_i$, an internal pressure at which the selected balloon unfolds and assumes an inflated shape sufficiently slowly to avoid generating vessel-damaging forces during unfolding and/or initial inflation stages of the balloon;
    raising the internal pressure of the selected balloon to the first treatment pressure $P_{min}$, a minimum therapeutic pressure sufficient to initiate disruption of the lesion without damaging the vessel lumen; and
    removing any remaining secondary lesions by reconfiguring the balloon catheter to produce shorter inflated balloon lengths and using internal balloon pressures higher than $P_{min}$.

2. The method of claim 1 wherein $P_i$ is less than $P_{min}$ and $P_{min}$ is less than a maximum useable internal balloon pressure, $P_{max}$.

3. The method of claim 1 wherein preparing the patient to receive the adjustable-balloon-length balloon catheter further comprises inserting a guidewire into the vessel lumen past the lesion.

4. The method of claim 1 wherein removing remaining secondary lesions by reconfiguring the balloon catheter to produce shorter inflated balloon length and internal pressures higher than $P_{min}$ further comprises:
    reducing the internal pressure of the selected balloon to a pressure at or below $P_i$;
    for each set of one or more remaining secondary lesions that can be treated in a next balloon-positioning-and-inflation cycle,
        adjusting the length of the selected balloon, while maintaining the internal balloon pressure below $P_i$, so that, when the internal pressure of the selected balloon is subsequently raised to a next treatment pressure higher than the first treatment pressure, the length of the selected balloon will be greater than a minimum inflation length but, when possible, less than or equal to the length of the set of one or more remaining secondary lesions;
        centering the selected balloon within a portion of a vessel lumen containing the set of one or more remaining secondary lesions; and
        raising the internal pressure of the selected balloon to the next treatment pressure.

5. The method of claim 4 wherein removing remaining secondary lesions by selecting additional balloon catheters with shorter inflated balloon lengths and by using internal pressures higher than $P_{min}$ further comprises:
    reducing the internal pressure of the balloon to a pressure at or below $P_1$ and removing the balloon catheter;
    for each set of one or more remaining secondary lesions that can be treated in a next balloon-positioning-and-inflation cycle,
        selecting a next balloon catheter with a next balloon length so that, when the internal pressure of a selected balloon with the next balloon length is subsequently raised to a next treatment pressure higher than the first treatment pressure, the length of the selected balloon will be either a minimum inflation length or, when possible, less than or equal to the length of the set of one or more remaining secondary lesions;
        centering the selected balloon within a portion of a vessel lumen containing the set of one or more remaining secondary lesions; and
        raisin the internal pressure of the selected balloon to the next treatment pressure.

6. A method that treats a lesion within a vessel lumen of a patient, the method comprising:

selecting a balloon catheter with a balloon of a length that does not exceed the length of the lesion when the balloon is inflated to a first treatment pressure;

preparing the patient to receive the balloon catheter;

centering the deflated balloon at the distal end of the balloon catheter within a portion of a vessel lumen containing the lesion;

raising the internal pressure of the balloon to P an internal pressure at which the balloon unfolds and assumes an inflated shape, sufficiently slowly to avoid generating vessel-damaging forces during unfolding and/or initial inflation stages of the balloon;

raising the internal pressure of the balloon to the first treatment pressure of $P_{min}$, a minimum therapeutic pressure sufficient to initiate disruption of the lesion without damaging the vessel lumen; and removing remaining secondary lesions by selecting additional balloon catheters with shorter inflated balloon lengths and by using internal balloon pressures higher than $P_{min}$.

7. The method of claim 6 wherein $P_i$ is less than $P_{min}$ and $P_{min}$ is less than a maximum allowable internal balloon pressure, $P_{max}$.

8. The method of claim 6 wherein preparing the patient to receive the adjustable-balloon-length balloon catheter further comprises inserting a guidewire into the vessel lumen past the lesion.

9. A method that treats lesions in a patient using balloon catheters, the method comprising:

for each lesion in a set of one or more primary lesions within a vessel lumen,
selecting a balloon catheter and configuration so that, when a balloon of the selected balloon catheter is inflated to a minimum therapeutic pressure sufficient to disrupt the lesion without damaging the vessel lumen, $P_{min}$, which is less than a maximum useable internal pressure for the balloon, $P_{max}$, and greater than an internal pressure at which the balloon unfolds and assumes an inflated shape, $P_i$, the length of the balloon does not exceed the length of the lesion;

centering the balloon of the selected balloon catheter within a portion of the vessel lumen containing the lesion;

raising the internal pressure of the balloon to $P_{min}$;

evaluating any remaining secondary lesions; and treating the remaining secondary lesions with selected balloon catheters and configurations with shorter inflated-balloon lengths and using internal balloon pressures greater than $P_{min}$.

10. The method of claim 9 further including:

receiving information about one or more lesions to be treated;

evaluating the received information to partition the lesions to be treated into one or more sets, each set including one or more primary lesions to be each treated during a separate procedure; and treating each set of primary lesions by the method of claim 1.

11. The method of claim 10 wherein the received information includes:

information about morphologies and dimensions of the one or more lesions to be treated;

information about a patient with the lesions to be treated; and information about available instrumentation and procedural capabilities for treating the lesions.

12. The method of claim 11 wherein the received information and information about treatment facilities and practitioners is used to schedule treatment of each set of one or more primary lesions.

13. The method of claim 9 further comprising:

representing the one or more primary lesions as a list, each element of in the list describing a primary lesion;

for each element in the list,
using information contained in the element, including a description of the lesion represented by the element, information about a patient with the lesion represented by the element, and information about the available instrumentation and procedural capabilities, to select the balloon catheter and configuration, including $P_{min}$, and to store indications of the selected balloon catheter and configuration in the element; and treating each lesion represented by an element in the list.

14. The method of claim 13 wherein selecting the balloon catheter and configuration, including $P_{min}$, may include one or more of:

selecting a balloon-length-adjustable balloon catheter, a length of the balloon to expose to an internal environment of the vessel lumen, and $P_{min}$ for the length of the balloon to expose to the internal environment of the vessel lumen; and selecting a balloon catheter, a balloon, and $P_{min}$ for the balloon.

15. The method of claim 14 wherein selecting a balloon-length-adjustable balloon catheter includes selecting a previously selected balloon-length-adjustable balloon catheter, a length of the balloon to expose to the internal environment of the vessel lumen, and a $P_{min}$ corresponding to the selected length of the balloon to expose to the internal environment of the vessel lumen.

16. The method of claim 13 wherein treating the lesions in the list further comprises:

while the list includes at least one entry,
using the descriptions of the lesions in the elements of the list, the additional available information to order the list, and available information about previous lesion treatment to order the list;

selecting one or more elements from the list, including a first element of the list;

treating the lesions described by the selected one or more elements according to information contained in the one or more elements;

removing the one or more selected elements from the list;

when one or more secondary lesions remains following treatment of the lesion corresponding to the selected one or more selected elements,
for each remaining secondary lesion,
adding an element to the list for the remaining secondary lesion, the added element including an indication of the remaining secondary lesion and a selected balloon catheter and configuration, including a treatment pressure.

17. The method of claim 16 wherein selecting the one or more elements from the list further includes:

when the first element describes a primary lesion, selecting only the first element from the list and treating the primary lesion with an internal balloon pressure equal to the $P_{min}$ included in the first list element; and when the first element describes a secondary lesion, when one or more additional elements in the list describe secondary lesions that can be treated together with the lesion described by the first element, selecting the first element and one or more additional elements along with a balloon catheter and configuration suitable for treating the lesions represented by the first element and one or more additional elements, including a treatment pressure equal to the largest treatment pressure in the first element and one or more additional elements, and otherwise selecting only the first element from the list.

18. The method of claim 16 wherein adding an element to the list for the remaining secondary lesion, the added element including an indication of the remaining secondary lesion and a selected balloon catheter and configuration, including a treatment pressure, further includes:

selecting a treatment pressure less than or equal to the $P_{max}$ for the selected balloon catheter and balloon length and greater than the last internal balloon pressure applied to the portion of the vessel lumen occupied by the remaining secondary lesion.

19. The method of claim 9 wherein raising the internal pressure of the balloon to $P_{min}$ further comprises:

raising the internal pressure of the balloon to $P_i$ sufficiently slowly to avoid generating vessel-damaging forces during unfolding and/or initial inflation stages of the balloon; and then raising the internal pressure of the balloon to $P_{min}$.

20. The method of claim 9 further comprising:

preparing the patient to receive one or more balloon catheters by inserting a guide wire into a vessel lumen past the furthest lesion from a guidewire entrypoint.

* * * * *